(12) United States Patent
Monrad et al.

(10) Patent No.: US 10,662,417 B2
(45) Date of Patent: May 26, 2020

(54) PECTATE LYASE VARIANTS AND POLYNUCLEOTIDES ENCODING SAME

(71) Applicant: NOVOZYMES A/S, Bagsvaerd (DK)

(72) Inventors: Rune Nygaard Monrad, Hillerød (DK); Peter Kamp Hansen, Lejre (DK); Frank Winther Rasmussen, Roskilde (DK); Anne Vindum Due, Bagsvaerd (DK); Jens Erik Nielsen, Bagsvaerd (DK); Garry Paul Gippert, København K (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 16/308,711

(22) PCT Filed: Jul. 5, 2017

(86) PCT No.: PCT/EP2017/066750
§ 371 (c)(1),
(2) Date: Dec. 10, 2018

(87) PCT Pub. No.: WO2018/007435
PCT Pub. Date: Jan. 11, 2018

(65) Prior Publication Data
US 2019/0194639 A1    Jun. 27, 2019

(30) Foreign Application Priority Data
Jul. 5, 2016  (EP) ..................... 16178069

(51) Int. Cl.
| | | |
|---|---|---|
| *C12N 9/88* | (2006.01) | |
| *C12Q 1/68* | (2018.01) | |
| *C12P 21/06* | (2006.01) | |
| *C07H 21/04* | (2006.01) | |
| *C11D 3/386* | (2006.01) | |

(52) U.S. Cl.
CPC ............ *C12N 9/88* (2013.01); *C11D 3/38636* (2013.01); *C12Y 402/02002* (2013.01)

(58) Field of Classification Search
CPC .. C12N 9/88; C12Q 1/68; C12P 21/06; C07H 21/04
See application file for complete search history.

(56) References Cited

U.S. PATENT DOCUMENTS

| | | |
|---|---|---|
| 6,124,127 A | 9/2000 | Andersen |
| 6,165,769 A | 12/2000 | Andersen |
| 6,172,030 B1 | 1/2001 | Wada |
| 6,187,580 B1 | 2/2001 | Andersen |
| 6,242,014 B1 | 6/2001 | Xu |
| 6,258,590 B1 | 7/2001 | Lange |
| 6,280,995 B1 | 8/2001 | Andersen |
| 6,284,524 B1 | 9/2001 | Andersen |
| 6,368,843 B1 | 4/2002 | Andersen |
| 6,399,351 B1 | 6/2002 | Bjoernvad |
| 6,429,000 B1 | 8/2002 | Andersen |
| 6,607,902 B2 | 8/2003 | Schroder Glad |
| 6,630,342 B2 | 10/2003 | Lange |
| 6,677,147 B2 | 1/2004 | Andersen |
| 6,808,915 B2 | 10/2004 | Schroder Glad |
| 7,144,722 B2 | 12/2006 | Andersen |
| 7,273,745 B2 | 9/2007 | Andersen |
| 7,601,529 B2 | 10/2009 | Glad |
| 7,611,882 B2 | 11/2009 | Bjoernave |
| 8,288,144 B2 * | 10/2012 | Glad ........................ C12N 9/88 435/232 |
| 8,563,290 B2 * | 10/2013 | Glad ........................ C12N 9/88 435/232 |
| 9,005,950 B2 * | 4/2015 | Glad ........................ C12N 9/88 435/232 |
| 2003/0175902 A1 | 9/2003 | Sloma |
| 2003/0175940 A1 | 9/2003 | Schroder Glad |
| 2005/0244922 A1 | 11/2005 | Andersen |
| 2005/0250181 A1 | 11/2005 | Schroder Glad |
| 2006/0165613 A1 | 7/2006 | Bjoernvad |

FOREIGN PATENT DOCUMENTS

| | | |
|---|---|---|
| CN | 103981167 A | 8/2014 |
| JP | 11318443 A | 11/1999 |
| JP | 2000253888 A | 9/2000 |
| JP | 2000262292 A | 9/2000 |
| WO | 98/06809 A1 | 2/1998 |
| WO | 98/45393 A2 | 10/1998 |
| WO | 99/27083 A1 | 6/1999 |
| WO | 99/27084 A1 | 6/1999 |
| WO | 00/29560 A1 | 5/2000 |
| WO | 00/37627 A1 | 6/2000 |
| WO | 00/42145 A1 | 7/2000 |

(Continued)

OTHER PUBLICATIONS

Ito et al, 2000, J Appl Glycosci 47(2), 243-251.
Kim et al, 1994, Biosci Biotech Biochem 58(5), 947-949.
Kim et al, 1994, Biosci Biotech Biochem 58(5), 947-949—Caplus Access No. 1994550110.
Kim et al, 1994, Biosci Biotech Biochem 58(5), 947-949—SQ alignment.
Kim et al, 2001, Protein Eng 14(5), 343-347—(Rel).pdf.
Nasser et al, 1990, Biochimie 72(9), 689-696.
Nasser et al, 1993, FEBS Letter 335(3), 319-326.
Nasser et al, 1990, Biochimie 72(9), 689-696—Biosis Access No. PREV199191043359.
Nasser et al, 1993, FEBS Lett 335(3), 319-326—Biosis Access No. PREV199497088806.

(Continued)

*Primary Examiner* — Maryam Monshipouri
(74) *Attorney, Agent, or Firm* — Kristin McNamara

(57) ABSTRACT

The present invention relates to pectate lyase variants exhibiting alterations relative to a parent enzyme exhibiting pectate lyase activity; to a method of producing such enzymes; and to methods for using such enzymes in the textile, detergent and cellulose fiber processing industries. Compared to the parent enzyme, the pectate lyase variants of the present invention exhibit improved stability in detergents.

17 Claims, No Drawings
Specification includes a Sequence Listing.

(56) References Cited

FOREIGN PATENT DOCUMENTS

| WO | 00/42155 A1 | 7/2000 |
| WO | 00/55309 A1 | 9/2000 |
| WO | 00/60063 A1 | 10/2000 |
| WO | 02/06442 A2 | 1/2002 |
| WO | 02/92741 A2 | 11/2002 |
| WO | 03/95638 A1 | 11/2003 |

OTHER PUBLICATIONS

Sakamoto et al, 1994, Biosci Biotech Biochem 58(2), 353-358.
Sakamoto et al, 1994, Biosci Biotech Biochem 58(2), 353-358—Biosis Access No. PREV199497268686.
CN 103981167—EBI Acces No. BBP52736 (2014).
CN 103981167—EBI Acces No. BBP53466 (2014).
JP 2000-253888—WPI Access No. 2000-642265 (2000).
JP 2000-262292—SQ alignment (2000).
JP 2000-262292—WPI Access No. 2000-659159 (2000).
WO 2002-006442 A2—SQ alignment (2002).
WO 2003-095638 A1—EBI Acces No. AXK82888 (2012).
WO 2003-095638 A1—EBI Acces No. AXK82897 (2012).
WO 2003-095638 A1—EBI Acces No. AXK82941 (2012).
WO 2003-095638 A1—EBI Acces No. AXK82951 (2012).
Anonymous, 2013, NCBI Reference sequence WP_008358433.1.
WO 2016-054222 A1—GSP-BCP028761.

\* cited by examiner

PECTATE LYASE VARIANTS AND POLYNUCLEOTIDES ENCODING SAME

CROSS-REFERENCE TO RELATED APPLICATIONS

This application is a 35 U.S.C. 371 national application of PCT/EP2017/066750 filed Jul. 5, 2017, which claims priority or the benefit under 35 U.S.C. 119 of European application 16178069.7 filed Jul. 5, 2016, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to pectate lyase variants exhibiting alterations relative to a parent enzyme; to a method of producing such enzymes; and to methods for using such enzymes in the textile, detergent and cellulose fiber processing industries. Compared to the parent enzyme, the pectate lyase variants of the present invention exhibit improved stability in detergents and/or improved thermal stability, e.g., in laundry processes and/or laundry and/or dishwash detergents.

Description of the Related Art

Pectin polymers are important constituents of plant cell walls. Pectin is a hetero-polysaccharide with a backbone composed of alternating homogalacturonan (smooth regions) and rhamnogalacturonan (hairy regions). The smooth regions are linear polymers of 1,4-linked alpha-D-galacturonic acid. The galacturonic acid residues can be methyl-esterified on the carboxyl group to a varying degree, usually in a non-random fashion with blocks of polygalacturonic acid being completely methyl-esterified.

Pectolytic enzymes (pectinases) can be classified according to their preferential substrate, highly methyl-esterified pectin or low methyl-esterified pectin and polygalacturonic acid (pectate), and their reaction mechanism, beta-elimination or hydrolysis. Pectinases can be mainly endo-acting, cutting the polymer at random sites within the chain to give a mixture of oligomers, or they may be exo-acting, attacking from one end of the polymer and producing monomers or dimers. Several pectinase activities acting on the smooth regions of pectin are included in the classification of enzymes provided by the Enzyme Nomenclature (1992) such as pectate lyase (EC 4.2.2.2), pectin lyase (EC 4.2.2.10), polygalacturonase (EC 3.2.1.15), exo-polygalacturonase (EC 3.2.1.67), exo-polygalacturonate lyase (EC 4.2.2.9) and exo-poly-alpha-galacturonosidase (EC 3.2.1.82).

Pectate lyases have been cloned from different bacterial genera such as *Erwinia, Pseudomonas, Klebsiella* and *Xanthomonas*. Also from *Bacillus subtilis* (Nasser et al. (1993) FEBS 335:319-326) and *Bacillus* sp. YA-14 (Kim et al. (1994) Biosci. Biotech. Biochem. 58:947-949) cloning of a pectate lyase has been described.

Variants of a pectate lyase from *Bacillus subtilis* have been disclosed in patent applications WO 2002/092741 and WO 2003/095638.

The pectate lyases are generally characterised by an alkaline pH optimum and an absolute requirement for divalent cations, $Ca^{2+}$ being the most stimulatory.

It is an object of the present invention to provide a cell-wall degrading enzyme variant, a pectin-degrading enzyme variant, especially a pectate lyase enzyme variant, which exhibits improved performance over the parent pectate lyase when applied e.g. in detergents or in textile industry processes.

SUMMARY OF THE INVENTION

The inventors have now found that certain amino acid substitutions in pectate lyases result in enzyme variants having improved performance and/or stability in the neutral or alkaline pH range compared to the parent enzyme, e.g., said performance and/or stability is particularly improved after and/or during storage. The pectate lyase variants of the invention, when used in detergent compositions, have improved storage stability i.e. lower sensitivity to detergent components or improved stability at high temperatures.

Thus, in some aspects the present invention relates to a pectate lyase variant comprising alterations at one or more positions selected from the group consisting of positions number: 250, 176, 124, 108, 149, and 325, wherein the alteration(s) are independently:

(i) an insertion of an amino acid downstream of the amino acid which occupies the position, (ii) a deletion of the amino acid which occupies the position, or (iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1.

In some aspects (e.g., any of the aspects mentioned above), the pectate lyase variant of the invention comprises one or more alterations at positions selected from the group consisting of positions: 250, 176, 124, 325, 108 and 149 (e.g., in the given order), e.g., most preferably the variant comprises an alteration at position 250, further preferably the variant comprises an alteration at position 176; further preferably the variant comprises an alteration at position 124; further preferably the variant comprises an alteration at position 325, further preferably the variant comprises an alteration at position 108, further preferably the variant comprises an alteration at position 149.

Such variant pectate lyase according to the one aspect preferably comprises one or more substitutions selected from the group consisting of: E108A, E108G, E108H, E108K, E108L, E108M, E108N, E108R, E108S, E108T, E108V, E108W, D124A, D124E, D124F, D124G, D124I, D124L, D124M, D124N, D124P, D124Q, D124R, D124S, D124T, D124V, D124W, D124Y, S149K, S149L, S149R, S149W, S176A, S176C, S176D, S176E, I250A, I250G, I250L, I250M, I250N, I250S, I250T, I325F, I325L, and I325Y.

Variants of the present invention may comprise further alterations; or may be variant pectate lyases according to another aspect, which preferably comprises one or more substitutions selected from the group consisting of: P48A, P48F, P48H, P48I, P48K, P48L, P48N, P48Q, P48R, P48S, P48T, P48W, P48Y, T49F, T49H, T49I, T49K, T49L, T49M, T49N, T49Q, T49R, T49V, T49W, T49Y, K99A, K99C, K99D, K99E, K99F, K99G, K99H, K99I, K99L, K99M, K99N, K99P, K99Q, K99S, K99T, K99V, K99W, K99Y, E108A, E108G, E108H, E108K, E108L, E108M, E108N, E108R, E108S, E108T, E108V, E108W, D124A, D124E, D124F, D124G, D124I, D124L, D124M, D124N, D124P, D124Q, D124R, D124S, D124T, D124V, D124W, S149K, S149L, S149R, S149W, S176A, S176C, S176D, S176E, S229I, S229K, S229L, S229M, S229Q, S229T, S229V, S229Y, I250A, I250G, I250L, I250M, I250N, I250S, I250T, K257A, K257C, K257D, K257H, K257I, K257L, K257M, K257Q, K257S, K257V, K257W, I325F, I325L, I325Y, Q356D, Q356E, Q356F, Q356G, Q356H, Q356I, Q356L, Q356N, Q356R, Q356T, Q356W, Q356Y, K99D+S176D+I325F, T49R+K99D+S176D+I325F+Q356F, T49R+K99D+S176D+K257L+I325F+Q356F, T49R+K99D+S176D+S229I+K257L+I325F+Q356F, K99D+S176D+I325F+Q356F, K99D+T49W+S176D+I325F+Q356F, K99D+D124W+S176D+I325F+Q356F, P48W+K99D+S176D+I325F+Q356F, K99D+E108N+S176D+I325F+Q356F, K99D+T49W+E108N+S176D+I325F+Q356F, P48W+S229I, S229I+K257L, S229I+I250N, S229I+Q356F, I250N+K257L, K257L+Q356F, P48W+I250N, P48W+Q356F, I250N+Q356F, P48W+T49R+K99D+S176D+K257L+I325F+Q356F, P48W+T49W+K99D+S176D+K257L+I325F+Q356F, T49R+K99D+D124W+S176D+K257L+I325F+Q356F, T49R+K99D+S176D+S229I+K257L+I325F+Q356F, S229I+I250N, S229I+Q356F, T49R+K99D+D124W+S176D+S229I+I250N+K257L+I325F+Q356F, T49R+K99D+S176D+S229I+K257L+I325F+Q356F, T49R+K99D+S176D+S229I+I250N+K257L+I325F+Q356F, T49R+K99D+D124W+S176D+S229I+I250N+K257L+I325F+Q356F, T49R+K99D+E108N+D124W+S176D+S229I+I250N+K257L+I325F+Q356F, P48W+T49R+K99D+S176D+I250N+K257L+I325F+Q356F, T49R+K99D+S176D+I250N+I325F+K257L+Q356F, P48W+S229I, S229I+K257L, S229I+I250N, S229I+Q356F, P48W+K257L, I250N+K257L, K257L+Q356F, P48W+I250N, P48W+Q356F, I250N+Q356F, and S229I+I250N+Q356F.

In another aspect the present invention relates to a variant of a parent enzyme having pectate lyase activity (EC 4.2.2.2) and comprising one or more substitutions selected from the group consisting of: P48A, P48F, P48H, P48I, P48K, P48L, P48N, P48Q, P48R, P48S, P48T, P48W, P48Y, T49F, T49H, T49I, T49K, T49L, T49M, T49N, T49Q, T49R, T49V, T49W, T49Y, K99A, K99C, K99D, K99E, K99F, K99G, K99H, K99I, K99L, K99M, K99N, K99P, K99Q, K99S, K99T, K99V, K99W, K99Y, E108A, E108G, E108H, E108K, E108L, E108M, E108N, E108R, E108S, E108T, E108V, E108W, D124A, D124E, D124F, D124G, D124I, D124L, D124M, D124N, D124P, D124Q, D124R, D124S, D124T, D124V, D124W, S149K, S149L, S149R, S149W, S176A, S176C, S176D, S176E, S229I, S229K, S229L, S229M, S229Q, S229T, S229V, S229Y, I250A, I250G, I250L, I250M, I250N, I250S, I250T, K257A, K257C, K257D, K257H, K257I, K257L, K257M, K257Q, K257S, K257V, K257W, I325F, I325L, I325Y, Q356D, Q356E, Q356F, Q356G, Q356H, Q356I, Q356L, Q356N, Q356R, Q356T, Q356W, Q356Y, K99D+S176D+I325F, T49R+K99D+S176D+I325F+Q356F, T49R+K99D+S176D+K257L+I325F+Q356F, T49R+K99D+S176D+S229I+K257L+I325F+Q356F, K99D+S176D+I325F+Q356F, K99D+T49W+S176D+I325F+Q356F, K99D+D124W+S176D+I325F+Q356F, P48W+K99D+S176D+I325F+Q356F, K99D+E108N+S176D+I325F+Q356F, K99D+T49W+E108N+S176D+I325F+Q356F, P48W+S229I, S229I+K257L, S229I+I250N, S229I+Q356F, I250N+K257L, K257L+Q356F, P48W+I250N, P48W+Q356F, I250N+Q356F, P48W+T49R+K99D+S176D+K257L+I325F+Q356F, P48W+T49W+K99D+S176D+K257L+I325F+Q356F, T49R+K99D+D124W+S176D+K257L+I325F+Q356F, I325F+Q356F, T49R+K99D+S176D+S229I+K257L+I325F+Q356F, S229I+I250N, S229I+Q356F, T49R+K99D+D124W+S176D+S229I+I250N+K257L+I325F+Q356F, T49R+K99D+S176D+S229I+K257L+I325F+Q356F, T49R+K99D+S176D+S229I+I250N+K257L+I325F+Q356F, T49R+K99D+D124W+S176D+S229I+I250N+K257L+I325F+Q356F, T49R+K99D+E108N+D124W+S176D+S229I+I250N+K257L+I325F+Q356F, P48W+T49R+K99D+S176D+I250N+K257L+I325F+Q356F, T49R+K99D+S176D+I250N+K257L+I325F+Q356F, T49R+K99D+S176D+I250N+I325F+K257L+Q356F, P48W+S229I, S229I+K257L, S229I+I250N, S229I+Q356F, P48W+K257L, I250N+K257L, K257L+Q356F, P48W+I250N, P48W+Q356F, I250N+Q356F, and S229I+I250N+Q356F, wherein each position corresponds to a position of the amino acid sequence of the pectate lyase having the amino acid sequence of SEQ ID NO:1 (e.g., using the numbering of SEQ ID NO:1), and wherein the variant has at least 75% identity to the amino acid sequence of SEQ ID NO:1.

In another aspect the present invention relates to a variant of a parent enzyme having pectate lyase activity (EC 4.2.2.2) and comprising one or more substitutions selected from the group consisting of substitutions described herein in i) Table 1 of Example 2, ii) Table 2 of Example 3, iii) Table 3 of Example 3, iv) Table 4 of Example 4, v) Table 5 of Example 5, wherein each position corresponds to a position of the amino acid sequence of the pectate lyase having the amino acid sequence of SEQ ID NO:1 (e.g., using the numbering of SEQ ID NO:1), and wherein the variant has at least 75% identity to the amino acid sequence of SEQ ID NO:1 or SEQ ID NO: 2.

In another aspect the present invention relates to a nucleic acid sequence encoding the pectate lyase variant.

In another aspect of the invention there is provided an expression vector.

In another aspect of the present invention there is provided a microbial host cell transformed with the abovementioned expression vector.

In another aspect of the present invention there is provided a method for improving the detergent stability of a pectate lyase, comprising altering one or more amino acids.

In another aspect of the invention there are provided methods for producing a pectate lyase variant according to the invention comprising culturing a cell into which has been introduced an expression vector as disclosed above, whereby said cell expresses the variant encoded by the nucleic acid sequence and recovering the pectate lyase variant.

The pectate lyase variant of the invention is useful for the treatment of cellulosic material, especially cellulose-containing fiber, yarn, woven or non-woven fabric, treatment of mechanical paper-making pulps or recycled waste paper, and for retting of fibres. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising a pectate lyase variant having substantial cell-wall degrading activity; and to use of the pectate lyase variant of the invention for the treatment e.g. cleaning of cellulose-containing fibers, yarn, woven or non-woven fabric. Further, additional aspects of the invention relates to an enzyme composition comprising the pectate lyase variant of the invention in combination with other enzymes, and to a cleaning or detergent composition, preferably a laundry or dish wash composition, comprising the pectate lyase variant of the invention.

The pectate lyase variant of the invention, is very effective for use in an enzymatic scouring process in the preparation of cellulosic material e.g. for proper response in subsequent dyeing operations.

Another aspect of the invention relates to the processing of wine and juice. The enzyme or enzyme preparation may be used in the treatment of mash from fruits and vegetables in order to improve the extractability or degradability of the mash.

Further, an aspect of the invention is the application as an animal feed additive. When added to feed containing plant material from soy bean, rape seed, lupin etc the pectate lyase variant significantly improves the in vivo break-down of plant cell wall material, whereby a better utilization of the plant nutrients by the animal is achieved.

Further, an aspect of the invention is the use of the variant of the invention for degrading of pectin-containing natural and processed food stains.

BRIEF DESCRIPTION OF THE SEQUENCES

SEQ ID NO: 1 shows the parent pectate lyase, on which the variants of the present invention are based. The parent pectate lyase is a variant of the pectate lyase from *Bacillus subtilis* disclosed in patent application WO 2002/092741.

SEQ ID NO: 2 shows a homolog polypeptide equally suitable as a parent pectate lyase (UNIPROT:Q6LEQ4—Kim, J et al. Biosci Biotechnol Biochem. 1994 58:947-949).
Definitions cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Corresponding to: The term "corresponding to" as used herein, refers to a way of determining the specific amino acid of a sequence wherein reference is made to a specific amino acid sequence. E.g. for the purposes of the present invention, when references are made to specific amino acid positions, the skilled person would be able to align another amino acid sequence to said amino acid sequence that reference has been made to, in order to determine which specific amino acid may be of interest in said another amino acid sequence. Alignment of another amino acid sequence with e.g. the mature sequence as set forth in SEQ ID NO: 1 or 2, or any other sequence listed herein, has been described elsewhere herein. Alternative alignment methods may be used, and are well-known for the skilled person.

Detergent stability" or "storage stability: The term "detergent stability" or "storage stability" is intended to mean the stability of the protein in a formulation containing detergents e.g. anionic surfactants. Anionic surfactants are characterized by the combination of an anionic group and a hydrophobic tail. When binding to the protein, a positively charged residue like Lysine or Arginine, and a hydrophobic area are thus likely interaction points. Similarly the dynamic of particularly flexible regions is opening up for the accessibility to amino acids normally buried in the internal of the protein. These residues are typically hydrophobic and are thus attractive for the tail of the surfactant. A chemical interaction between enzyme and surfactant will with high certainty leave the enzyme inactive. Thus improved detergent- or storage stability means that at a certain detergent concentration and temperature, a greater enzymatic activity will be retained after a certain period of time (greater residual activity).

Accordingly, thermostability and detergent stability are two independent characteristics of a protein or an enzyme.

The pectate lyase variants of the invention having improved detergent stability may exhibit at least 120% (preferably at least 140%, more preferably at least 160%, even more preferably at least 180%, even more preferably at least 200%, most preferably at least 250% and in particular at least 300%) residual activity compared to the parent pectate lyase, when subjected to the analysis method described in Examples 3 and/or 4.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Half-life improvement factor: the term "Half-life improvement factor" or "HIF" can be defined according to the following formula: HIF=T½(variant)/T½(reference polypeptide, e.g., a parent or a backbone polypeptide). A preferred way of calculating HIF is also described in example 2 below, which is incorporated by reference herein.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

Improved wash performance: The term "improved wash performance" is defined herein as a variant enzyme displaying an increased wash performance relative to the wash performance of a parent enzyme e.g. by increased stain removal. The term "improved wash performance" includes wash performance in laundry but also e.g. in hard surface cleaning such as automated dish wash (ADW).

Improved property: The term "improved property" means a characteristic associated with a variant that is improved compared to the parent. Such improved properties include, but are not limited to, detergent stability, e.g., stability in liquid detergent, chemical stability, oxidation stability, pH stability, stability under storage conditions.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc.

Modification: The term "modification", in the context of the polypeptides of the invention, means that one or more amino acids within the reference amino acid sequence (i.e. SEQ ID NOs: 1 or 2) are altered by substitution with a different amino acid, by insertion of an amino acid or by deletion, preferably by at least one deletion. The terms "modification", "alteration", and "mutation" may be used interchangeably and constitute the same meaning and purpose.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent pectate lyase: The term "parent" or "parent pectate lyase" means any polypeptide with pectate lyase activity to which an alteration is made to produce the enzyme variants of the present invention. A examplary parent pectate lyase is shown in SEQ ID NO:1. A homolog polypeptide equally suitable as a parent pectate lyase is known from Kim et al. (1994) Biosci. Biotech. Biochem. 58:947-949 (UNIPROT:Q6LEQ4).

Pectate lyase: The term "Pectate lyase" means an activity (EC 4.2.2.2) that catalyzes the eliminative cleavage of (1→4)-α-D-galacturonan to give oligosaccharides with 4-deoxy-α-D-galact-4-enuronosyl groups at their non-reducing ends.

For purposes of the present invention, pectate lyase activity may be determined according to the procedures described in the Methods, or the Examples 3 and/or 4. In one aspect, the variants of the present invention have at least 20%, e.g., at least 40%, at least 50%, at least 60%, at least 70%, at least 80%, at least 90%, at least 95%, or at least 100% of the pectate lyase activity of the mature polypeptide of SEQ ID NO: 1.

Pectin: The term "pectin" denotes pectate, polygalacturonic acid, and pectin which may be esterified to a higher or lower degree.

Pectinase: The term "pectinase" denotes a pectinase enzyme defined according to the art and includes an enzyme that cleaves poly- and/or oligosaccharide chains in pectic substances, e.g., poly(1,4-alpha-D-galacturonide) and its derivatives (see reference Sakai et al., Pectin, pectinase and protopectinase: production, properties and applications, pp 213-294 in: Advances in Applied Microbiology vol:39, 1993). Non-limiting examples of pectinases include hydrolase type pectinases (e.g. rhamnogalacturonan hydrolases) and lyase type pectinases (e.g., pectate lyases). Preferably a pectinase of the invention is a pectinase enzyme which catalyzes the random cleavage of alpha-1,4-glycosidic linkages in pectic acid also called polygalacturonic acid by transelimination such as the enzyme class polygalacturonate lyase (EC 4.2.2.2) (PGL) also known as poly(1,4-alpha-D-galacturonide) lyase also known as pectate lyase.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

Swatches: The term "swatches" means the textile used in the examples, which are obtained from Center for Testmaterials BV, P.O. Box 120, 3133 KT Vlaardingen, the Netherlands.

Variant: The term "variant" means a polypeptide having pectate lyase activity comprising an alteration, i.e., a substitution, insertion, and/or deletion, at one or more (e.g., several) positions.

A substitution means replacement of the amino acid occupying a position with a different amino acid; a deletion means removal of the amino acid occupying a position; and an insertion means adding an amino acid adjacent to and immediately following the amino acid occupying a position.

The variants of the present invention have at least 20%, e.g., at least 40%, at least 50%, at least 60%, at least 70%, at least 80%, at least 90%, at least 95%, or at least 100% of the pectate lyase activity of the mature polypeptide of SEQ ID NO: 1.

Wild-type pectate lyase: The term "wild-type pectate lyase" as used herein refers to a pectate lyase expressed by a naturally occurring microorganism, such as a bacterium, yeast, or filamentous fungus found in nature.

Conventions for Designation of Variants

For purposes of the present invention, the mature polypeptide disclosed in SEQ ID NO: 1 is used to determine the corresponding amino acid residue in another pectate lyase. The amino acid sequence of another pectate lyase is aligned with the mature polypeptide disclosed in SEQ ID NO: 1, and based on the alignment, the amino acid position number corresponding to any amino acid residue in the mature polypeptide disclosed in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another pectate lyase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position,*. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple Alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to variants of a parent pectate lyase (EC 4.2.2.2). The variants have improved properties compared to the parent enzyme, especially the detergent stability or storage stability in detergent compositions is improved.

In the process of improving the properties of the parent pectate lyase, the inventors found that alterations of specific amino acids in the parent polypeptide backbone would significantly alter the detergent stability of the produced variant.

Variants

In one aspect, the present invention provides pectate lyase variants, comprising an alteration at one or more positions selected from the group consisting of positions 250, 176, 124, 108, 149, and 325, wherein numbering is according to the mature polypeptide of SEQ ID NO: 1, and wherein the alteration(s) are independently:

(i) an insertion of an amino acid downstream of the amino acid which occupides the position;

(ii) a deletion of the amino acid which occupies the position; or (iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1.

In one embodiment, the pectate lyase variants comprises a substitution in one or more (e.g. several) positions corresponding to positions 250, 176, 124, 108, 149, and 325 wherein numbering is according to SEQ ID NO: 1, and wherein the variant has pectate lyase activity.

In a particular embodiment, the pectate lyase variant, comprises a substitution in the following positions: 250+124, 250+108, 250+149, 250+325, 176+124, 176+108, 176+149, 176+325, 124+108, 124+149, 124+325, 108+149, 108+325, 149+325, 250+176+124, 250+176+108, 250+176+149, 250+176+325, 250+124+108, 250+124+149, 250+124+325, 250+108+149, 250+108+325, 250+149+325, 176+124+108, 176+124+149, 176+124+325, 176+108+149, 176+108+325, 176+149+325, 124+108+149, 124+108+325, 124+149+325, 108+149+325, 250+176+124+108, 250+176+124+149, 250+176+124+325, 250+176+108+149, 250+176+108+325, 250+176+149+325, 250+124+108+149, 250+124+108+325, 250+124+149+325, 250+108+149+325, 176+124+108+149, 176+124+108+325, 176+124+149+325, 176+108+149+325, 124+108+149+325, 250+176+124+108+149, 250+176+124+108+325, 250+176+124+149+325, 250+176+108+149+325, 250+124+108+149+325, 176+124+108+149+325, and 250+176+124+108+149+325, wherein numbering is according to the mature polypeptide SEQ ID NO: 1 and wherein the variant has pectate lyase activity.

In another aspect, the present invention provides pectate lyase variants, comprising a substitution at one or more (e.g., several) positions corresponding to positions 48, 49, 99, 108, 124, 149, 176, 229, 250, 257, 325, and 356 (e.g., numbering relative to SEQ ID NO:1), wherein the variant has pectate lyase activity.

In one embodiment, the pectate lyase variants comprises a substitution in the following positions: 48+49, 48+99, 48+108, 48+124, 48+149, 48+176, 48+229, 48+250, 48+257, 48+325, 48+356, 49+99, 49+108, 49+124, 49+149, 49+176, 49+229, 49+250, 49+257, 49+325, 49+356, 99+108, 99+124, 99+149, 99+176, 99+229, 99+250, 99+257, 99+325, 99+356, 108+124, 108+149, 108+176, 108+229, 108+250, 108+257, 108+325, 108+356, 124+149, 124+176, 124+229, 124+250, 124+257, 124+325, 124+356, 149+176, 149+229, 149+250, 149+257, 149+325, 149+356, 176+229, 176+250, 176+257, 176+325, 176+356, 229+250, 229+257, 229+325, 229+356, 250+257, 250+325, 250+356, 257+325, 257+356, 325+356, 48+49+99, 48+49+108, 48+49+124, 48+49+149, 48+49+176, 48+49+229, 48+49+250, 48+49+257, 48+49+325, 48+49+356, 48+99+108, 48+99+124, 48+99+149, 48+99+176, 48+99+229, 48+99+250, 48+99+257, 48+99+325, 48+99+356, 48+108+124, 48+108+149, 48+108+176, 48+108+229, 48+108+250, 48+108+257, 48+108+325, 48+108+356, 48+124+149, 48+124+176, 48+124+229, 48+124+250, 48+124+257, 48+124+325, 48+124+356, 48+149+176, 48+149+229, 48+149+250, 48+149+257, 48+149+325, 48+149+356, 48+176+229, 48+176+250, 48+176+257, 48+176+325, 48+176+356, 48+229+250, 48+229+257, 48+229+325, 48+229+356, 48+250+257, 48+250+325, 48+250+356, 48+257+325, 48+257+356, 48+325+356, 49+99+108, 49+99+124, 49+99+149, 49+99+176, 49+99+229, 49+99+250, 49+99+257, 49+99+325, 49+99+356, 49+108+124, 49+108+149, 49+108+176, 49+108+229, 49+108+250, 49+108+257, 49+108+325, 49+108+356, 49+124+149, 49+124+176, 49+124+229, 49+124+250, 49+124+257, 49+124+325, 49+124+356, 49+149+176, 49+149+229, 49+149+250, 49+149+257, 49+149+325, 49+149+356, 49+176+229, 49+176+250, 49+176+257 49+176+325, 49+176+356, 49+229+250, 49+229+257, 49+229+325, 49+229+356, 49+250+257, 49+250+325, 49+250+356, 49+257+325, 49+257+356, 49+325+356, 99+108+124, 99+108+149, 99+108+176, 99+108+229, 99+108+250, 99+108+257, 99+108+325, 99+108+356, 99+124+149, 99+124+176, 99+124+229, 99+124+250, 99+124+257, 99+124+325, 99+124+356, 99+149+176, 99+149+229, 99+149+250, 99+149+257, 99+149+325, 99+149+356, 99+176+229, 99+176+250, 99+176+257, 99+176+325, 99+176+356, 99+229+250, 99+229+257, 99+229+325, 99+229+356, 99+250+257, 99+250+325, 99+250+356, 99+257+325, 99+257+356, 99+325+356, 108+124+149, 108+124+176, 108+124+229, 108+124+250, 108+124+257, 108+124+325, 108+124+356, 108+149+176, 108+149+229, 108+149+250, 108+149+257, 108+149+325, 108+149+356, 108+176+229, 108+176+250, 108+176+257, 108+176+325, 108+176+356, 108+229+250, 108+229+257, 108+229+325, 108+229+356, 108+250+257, 108+250+325, 108+250+356, 108+257+325, 108+257+356, 108+325+356, 124+149+176, 124+149+229, 124+149+250, 124+149+257, 124+149+325, 124+149+356, 124+176+229, 124+176+250, 124+176+257, 124+176+325, 124+176+356, 124+229+250, 124+229+257, 124+229+325, 124+229+356, 124+250+257, 124+250+325, 124+250+356, 124+257+325, 124+257+356, 124+325+356, 149+176+229, 149+176+250, 149+176+257, 149+176+325, 149+176+356, 149+229+250, 149+229+257, 149+229+325, 149+229+356, 149+250+257, 149+250+325, 149+250+356, 149+257+325, 149+257+356, 149+325+356, 176+229+250, 176+229+257, 176+229+325, 176+229+356, 176+250+257, 176+250+325, 176+250+356, 176+257+325, 176+257+356, 176+325+356, 229+250+257, 229+250+325, 229+250+356, 229+257+325, 229+257+356, 229+325+356, 250+257+325, 250+257+356, 250+325+356, and 257+325+356, wherein numbering is according to the mature polypeptide of SEQ ID NO: 1, and the variant has pectate lyase activity.

The present invention further provides pectate lyase variants, comprising a substitution (or substitutions) at one or more (e.g., several) positions corresponding to positions: 48, 49, 99, 108, 124, 149, 176, 229, 250, 257, 325, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+176+229+257+325+356, 229+250, 229+356, 49+99+124+176+229+250+257+325+356, 49+99+176+229+257+325+356, 49+99+176+229+250+257+325+356, 49+99+124+176+229+250+257+325+356, 49+99+108+124+176+229+250+257+325+356, 48+49+99+176+250+257+325+356, 49+99+176+250+325+257+356, 48+229, 229+257, 229+250, 229+356, 48+257, 250+257, 257+356, 48+250, 48+356, 250+356, 229+250+356 (e.g., numbering relative to SEQ ID NO:1), wherein the variant has pectate lyase activity.

In a preferred embodiment the variant comprises a substitution to a amino acid carrying positive charges, i.e., to lysine or arginine, in one or more of positions 48, 49, 108, 124 and 149 (e.g., numbering according to SEQ ID NO:1). Preferred variants of the present invention thus comprise variants in which the overall charge of the enzyme has been made more positive by a substitution in one or more of positions 48, 49, 108, 124 and 149 (e.g., numbering according to SEQ ID NO:1).

In an embodiment, the variant has a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent pectate lyase.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 1 or SEQ ID NO: 2.

In another embodiment, the parent has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 1 or SEQ ID NO: 2.

In one aspect, the number of alterations in the variants of the present invention is 1-20, e.g., 1-10 and 1-5, such as 1, 2, 3, 4, 5, 6, 7, 8, 9, 10, 11, 12 or 13 alterations.

In another aspect, the variant comprises a substitution at a position corresponding to position 48. Preferably, the amino acid at a position corresponding to position 48 is substituted with Ala, Phe, His, Ile, Lys, Leu, Arg, Ser, Thr, Trp, or Tyr, preferably with Arg, Lys or Thr.

In another aspect, the variant comprises a substitution at a position corresponding to position 49. Preferably, the amino acid at a position corresponding to position 49 is substituted with Phe, His, Ile, Lys, Leu, Met, Asn, Gln, Arg, Val, Trp, or Tyr, preferably with Arg, Lys or Trp.

In another aspect, the variant comprises a substitution at a position corresponding to position 99. Preferably, the amino acid at a position corresponding to position 99 is substituted with Ala, Cys, Asp, Glu, Phe, Gly, His, Ile, Leu, Met, Asn, Pro, Gln, Ser, Thr, Val, Trp, or Tyr, preferably with Cys or Glu or Asp.

In another aspect, the variant comprises a substitution at a position corresponding to position 108. Preferably, the amino acid at a position corresponding to position 108 is substituted with Ala, Gly, His, Lys, Leu, Met, Asn, Arg, Ser, Thr, Val, or Trp, preferably with Lys, Asn or Arg.

In another aspect, the variant comprises a substitution at a position corresponding to position 124. Preferably, the amino acid at a position corresponding to position 124 is substituted with Ala, Glu, Phe, Gly, Ile, Leu, Met, Asn, Pro, Gln, Arg, Ser, Thr, Val, Trp, or Tyr, preferably with Arg, or Trp.

In another aspect, the variant comprises a substitution at a position corresponding to position 149. Preferably, the amino acid at a position corresponding to position 149 is substituted with Lys, Leu, Arg, or Trp, preferably with Lys or Arg.

In another aspect, the variant comprises a substitution at a position corresponding to position 176. Preferably, the amino acid at a position corresponding to position 176 is substituted with Ala, Cys, Asp, or Glu, preferably with Cys or Asp.

In another aspect, the variant comprises a substitution at a position corresponding to position 229. Preferably, the amino acid at a position corresponding to position 229 is substituted with Ile, Lys, Leu, Met, Asn, Gln, Val, Thr, or Tyr, preferably with Ile, Lys, Tyr or Val.

In another aspect, the variant comprises a substitution at a position corresponding to position 250. Preferably, the amino acid at a position corresponding to position 250 is substituted with Ala, Gly, Leu, Met, Asn, Ser, or Thr, preferably with Leu, Asn or Thr.

In another aspect, the variant comprises a substitution at a position corresponding to position 257. Preferably, the amino acid at a position corresponding to position 257 is substituted with Ala, Cys, Asp, His, Ile, Leu, Met, Gln, Ser, Val, or Trp, preferably with Leu, Met, Gln, His, Cys or Asp.

In another aspect, the variant comprises a substitution at a position corresponding to position 325. Preferably, the amino acid at a position corresponding to position 325 is substituted with Phe, Leu, or Tyr, preferably with Phe.

In another aspect, the variant comprises a substitution at a position corresponding to position 356. Preferably, the amino acid at a position corresponding to position 356 is substituted with Asp, Glu, Phe, Gly, Ile, Leu, Asn, Arg, Thr, Trp, or Tyr, preferably with Glu or Phe.

Such variant pectate lyase preferably comprises one or more substitutions selected from the group consisting of: P48A, P48F, P48H, P48I, P48K, P48L, P48N, P48Q, P48R, P48S, P48T, P48W, P48Y, T49F, T49H, T49I, T49K, T49L, T49M, T49N, T49Q, T49R, T49V, T49W, T49Y, K99A, K99C, K99D, K99E, K99F, K99G, K99H, K99I, K99L, K99M, K99N, K99P, K99Q, K99S, K99T, K99V, K99W, K99Y, E108A, E108G, E108H, E108K, E108L, E108M, E108N, E108R, E108S, E108T, E108V, E108W, D124A, D124E, D124F, D124G, D124I, D124L, D124M, D124N, D124P, D124Q, D124R, D124S, D124T, D124V, D124W, S149K, S149L, S149R, S149W, S176A, S176C, S176D, S176E, S229I, S229K, S229L, S229M, S229Q, S229T, S229V, S229Y, I250A, I250G, I250L, I250M, I250N, I250S, I250T, K257A, K257C, K257D, K257H, K257I, K257L, K257M, K257Q, K257S, K257V, K257W, I325F, I325L, I325Y, Q356D, Q356E, Q356F, Q356G, Q356H, Q356I, Q356L, Q356N, Q356R, Q356T, Q356W, Q356Y, K99D+ S176D+I325F, T49R+K99D+S176D+I325F+Q356F, T49R+K99D+S176D+K257L+I325F+Q356F, T49R+ K99D+S176D+S229I+K257L+I325F+Q356F, K99D+ S176D+I325F+Q356F, K99D+T49W+S176D+I325F+ Q356F, K99D+D124W+S176D+I325F+Q356F, P48W+ K99D+S176D+I325F+Q356F, K99D+E108N+S176D+ I325F+Q356F, K99D+T49W+E108N+S176D+I325F+ Q356F, P48W+S229I, S229I+K257L, S229I+I250N, S229I+Q356F, I250N+K257L, K257L+Q356F, P48W+ I250N, P48W+Q356F, I250N+Q356F, P48W+T49R+ K99D+S176D+K257L+I325F+Q356F, P48W+T49W+ K99D+S176D+K257L+I325F+Q356F, T49R+K99D+ D124W+S176D+K257L+I325F+Q356F, T49R+K99D+ S176D+S229I+K257L+I325F+Q356F, S229I+I250N, S229I+Q356F, T49R+K99D+D124W+S176D+S229I+ I250N+K257L+I325F+Q356F, T49R+K99D+S176D+ S229I+K257L+I325F+Q356F, T49R+K99D+S176D+ S229I+I250N+K257L+I325F+Q356F, T49R+K99D+ D124W+S176D+S229I+I250N+K257L+I325F+Q356F, T49R+K99D+E108N+D124W+S176D+S229I+I250N+ K257L+I325F+Q356F, P48W+T49R+K99D+S176D+ I250N+K257L+I325F+Q356F, T49R+K99D+S176D+ I250N+I325F+K257L+Q356F, P48W+S229I, S229I+ K257L, S229I+I250N, S229I+Q356F, P48W+K257L, I250N+K257L, K257L+Q356F, P48W+I250N, P48W+ Q356F I250N+Q356F, and S229I+I250N+Q356F, wherein each position corresponds to a position of the amino acid sequence of the pectate lyase having the amino acid sequence of SEQ ID NO:1, and wherein the variant has at least 75% identity to the amino acid sequence of SEQ ID NO:1.

More preferably the variant pectate lyase comprises one or more substitutions selected from the group consisting of: S229I, I250L, T49R, S229V, S229K, I250N, and I250T.

Even more preferably the variant pectate lyase comprises one or both substitutions selected from the group consisting of S229I and I250N. Accordingly, in one embodiment, the pectate lyase variant comprises or consists of the substitutions selected from the group consisting of: S229I+I250L, S229I+I250N, S229I+I250T, I250L+S229V, I250L+S229K, S229V+I250N, S229V+I250T, S229K+I250N, and S229K+ I250T, wherein numbering is according to the mature polypeptide of SEQ ID NO: 1, and the variant has pectate lyase activity.

In another aspect, the variant comprises or consists of alterations at positions corresponding to positions 48 and 229, such as those described above.

In another aspect, the variant comprises or consists of alterations at positions corresponding to positions 49 and 229, such as those described above. Accordingly, in one embodiment, the pectate lyase variant comprises or consists of the substitutions selected from the group consisting of: S229I+T49R, T49R+S229V, and T49R+S229K, wherein numbering is according to the mature polypeptide of SEQ ID NO: 1, and the variant has pectate lyase activity.

In another aspect, the variant comprises or consists of alterations at positions corresponding to positions 48 and 250, such as those described above. Accordingly, in one embodiment, the pectate lyase variant comprises or consists of the substitutions selected from the group consisting of: I250L+T49R, T49R+I250N, and T49R+I250T, wherein numbering is according to the mature polypeptide of SEQ ID NO: 1, and the variant has pectate lyase activity.

In another aspect, the variant comprises or consists of alterations at positions corresponding to positions 229 and 257, such as those described above.

In another aspect, the variant comprises or consists of alterations at positions corresponding to positions 229 and 250, such as those described above.

In another aspect, the variant comprises or consists of alterations at positions corresponding to positions 229 and 356, such as those described above.

In another aspect, the variant comprises or consists of alterations at positions corresponding to positions 250 and 257, such as those described above.

In another aspect, the variant comprises or consists of alterations at positions corresponding to positions 49, 99, 176, 229, 257, 325 and 356 such as those described above.

In another aspect, the variant comprises or consists of alterations at positions corresponding to positions 49, 99, 176, 229, 250, 257, 325 and 356 such as those described above.

In a preferred aspect, the variant comprises one or more substitutions selected from the group consisting of 49R, 99D, 108N/K/R, 124R, 149K/R, 229I/V/Y, 250L/N/T, 257C/ D/H/M/Q, and 325F.

It is at present contemplated that one or more of these substitutions either alone or in combination increase the detergent stability of the pectate lyase variant when compared to the parent enzyme.

Preferred multiple substitutions which increase the detergent stability of a variant pectate lyase include: P48W+ S229I, S229I+K257L, S229I+I250N, S229I+Q356F, P48W+K257L, I250N+K257L, K257L+Q356F, P48W+ I250N, P48W+Q356F, I250N+Q356F, K99D+S176D+ I325F, T49R+K99D+S176D+I325F+Q356F, T49R+K99D+ S176D+K257L+I325F+Q356F, T49R+K99D+S176D+ S229I+K257L+I325F+Q356F, K99D+S176D+I325F+ Q356F, K99D+T49W+S176D+I325F+Q356F, K99D+ D124W+S176D+I325F+Q356F, P48W+K99D+S176D+ I325F+Q356F, K99D+E108N+S176D+I325F+Q356F, K99D+T49W+E108N+S176D+I325F+Q356F, P48W+ T49R+K99D+S176D+I250N+K257L+I325F+Q356F, T49R+K99D+S176D+S229I+I250N+K257L+I325F+ Q356F, T49R+K99D+D124W+S176D+S229I+I250N+ K257L+I325F+Q356F, T49R+K99D+E108N+D124W+ S176D+S229I+I250N+K257L+I325F+Q356F, T49R+ K99D+S176D+I250N+I325F+K257L+Q356F, P48W+ T49R+K99D+S176D+K257L+I325F+Q356F, P48W+ T49W+K99D+S176D+K257L+I325F+Q356F T49R+ K99D+D124W+S176D+K257L+I325F+Q356F and S229I+ I250N+Q356F, and wherein each position corresponds to a position of the amino acid sequence of the pectate lyase having the amino acid sequence of SEQ ID NO:1, and wherein the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1 which has pectate lyase activity.

More preferred multiple substitutions which increase the detergent stability include: T49R+K99D+S176D+S229I+ K257L+I325F+Q356F, T49R+K99D+S176D+S229I+ I250N+K257L+I325F+Q356F, T49R+K99D+D124W+

S176D+S229I+I250N+K257L+I325F+Q356F, T49R+K99D+S176D+I250N+I325F+K257L+Q356F, P48W+S229I, S229I+K257L, S229I+I250N, S229+1 Q356F, I250N+K257L, P48W+I250N, and I250N+Q356F.

Even more preferred, the variant comprises a combination of substitutions selected from the group consisting of: T49R+K99D+S176D+S229I+K257L+I325F+Q356F, T49R+K99D+S176D+S229I+I250N+K257L+I325F+Q356F, S229I+I250N, and S229I+Q356F.

In an aspect, the variant comprises or consists of the substitution S299I of the mature polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1 which has pectate lyase activity, and further the variant has improved stability compared to the mature pectate lyase of SEQ ID NO: 1. In this aspect, the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1.

In an aspect, the variant comprises or consists of the substitution I250N of the mature polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1 which has pectate lyase activity, and further the variant has improved stability compared to the mature pectate lyase of SEQ ID NO: 1. In this aspect, the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1.

In another aspect, the variant comprises or consists of T49R+K99D+S176D+S229I+K257L+I325F+Q356F of the mature polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1 which has pectate lyase activity, and further the variant has improved stability compared to the mature pectate lyase of SEQ ID NO: 1. In this aspect, the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1.

In another aspect, the variant comprises or consists of the substitutions T49R+K99D+S176D+S229I+I250N+K257L+I325F+Q356F of the mature polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1 which has pectate lyase activity, and further the variant has improved stability compared to the mature pectate lyase of SEQ ID NO: 1. In this aspect, the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1.

In another aspect, the variant comprises or consists of the substitutions S229I+I250N of the mature polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1 which has pectate lyase activity, and further the variant has improved stability compared to the mature pectate lyase of SEQ ID NO: 1. In this aspect, the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1.

In another aspect, the variant comprises or consists of the substitutions S229I+Q356F of the mature polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1 which has pectate lyase activity, and further the variant has improved stability compared to the mature pectate lyase of SEQ ID NO: 1. In this aspect, the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1.

The variant may further comprise one or more additional substitutions selected from the group consisting of: 1, 2, 3, 4, 6, 7, 8, 10, 12, 13, 14, 15, 16, 17, 18, 19, 20, 21, 22, 23, 24, 25, 27, 29, 32, 33, 34, 35, 36, 38, 39, 41, 42, 43, 44, 53, 55, 56, 57, 58, 59, 60, 62, 63, 65, 66, 67, 72, 73, 77, 78, 80, 81, 82, 83, 84, 85, 88, 89, 90, 92, 93, 94, 95, 96, 97, 98, 100, 101, 102, 103, 104, 108, 109, 110, 112, 113, 114, 117, 119, 120, 121, 124, 125, 126, 127, 128, 129, 130, 131, 132, 133, 135, 137, 138, 142, 143, 144, 145, 147, 149, 150, 151, 152, 153, 154, 155, 157, 159, 160, 161, 162, 163, 164, 165, 166, 167, 168, 169, 171, 172, 173, 174, 175, 176, 177, 178, 179, 180, 181, 183, 184, 187, 188, 190, 191, 192, 195, 197, 198, 200, 203, 205, 205, 207, 208, 209, 210, 211, 212, 214, 216, 217, 219, 220, 221, 222, 223, 225, 226, 227, 230, 231, 232, 233, 236, 238, 239, 240, 241, 242, 243, 244, 245, 246, 247, 248, 249, 250, 252, 253, 254, 255, 259, 260, 261, 262, 263, 364. 265, 266, 267, 268, 269, 270, 271, 273, 274, 275, 276, 278, 279, 280, 281, 282, 283, 284, 285, 287, 288, 289, 290, 291, 292, 293, 294, 296, 297, 299, 300, 304, 306, 309, 310, 311, 312, 313, 315, 317, 318, 319, 320, 321, 322, 325, 327, 328, 329, 330, 342, 343, 344, 345, 346, 347, 348, 350, 351, 352, 353, 354, 355, 358, 359, 360, 361, 362, 364, 365, 367, 368, 369, 370, 371, 372, 373, 374, 375, 376, 377, 379, 380, 382, 383, 385, 386, 388, 390, 392, 394, 395, 396, 398 and 399 of the mature polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1 which has pectate lyase activity, and further the variant has improved stability compared to the mature pectate lyase of SEQ ID NO: 1.

The variant may also comprise one or more additional substitutions selected from the group consisting of: 5, 9, 11, 26, 28, 30, 31, 37, 40, 45, 46, 47, 48, 49, 50, 51, 52, 54, 61, 64, 68, 69, 70, 71, 74, 75, 76, 79, 86, 87, 91, 99, 105, 106, 107, 111, 115, 116, 118, 122, 123, 134, 136, 139, 140, 141, 146, 148, 156, 158, 170, 182, 185, 186, 189, 193, 194, 196, 199, 201, 202, 204, 213, 215, 218, 224, 228, 229, 234, 235, 237, 251, 256, 257, 258, 272, 277, 286, 295, 298, 301, 302, 303, 305, 307, 308, 314, 316, 323, 324, 326, 331, 332, 333, 334, 335, 336, 337, 338, 339, 340, 341, 349, 356, 357, 363, 366, 378, 381, 384, 386, 387, 389, 390, 391, 393 and 397 of the mature polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 1 which has pectate lyase activity, and further the variant has improved stability compared to the mature pectate lyase of SEQ ID NO: 1.

Such additional substitutions may also include amino acid changes of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like. Such additional substitutions significantly affecting the variants properties include those disclosed in patent applications WO 2002/092741 and WO 2003/095638.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for pectate lyase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The pectate lyase in SEQ ID NO: 1 is used as an example for one parent enzyme. The parent pectate lyase may be (a) a polypeptide having a sequence identity to the mature polypeptide of SEQ ID NO: 1 at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have pectate lyase activity. In a particular embodiment, the parent enzyme is a parent pectate lyase having at least 96% sequence identity to the mature polypeptide of SEQ ID NO: 1. In one aspect, the amino acid sequence of the parent differs by up to 10 amino acids, e.g., 1, 2, 3, 4, 5, 6, 7, 8, 9, or 10, from the mature polypeptide of SEQ ID NO: 1.

In another aspect, the parent comprises or consists of the amino acid sequence of SEQ ID NO: 1. In another aspect, the parent comprises or consists of the mature polypeptide of SEQ ID NO: 1.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial pectate lyase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* pectate lyase, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* pectate lyase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis,*

*Bacillus megaterium, Bacillus pumilus, Bacillus stearothermophilus, Bacillus subtilis*, or *Bacillus thuringiensis* pectate lyase.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having pectate lyase activity, comprising: (a) introducing into a parent pectate lyase (e.g., having SEQ ID NO:1 or SEQ ID NO: 2) a substitution at one or more (e.g., several) positions corresponding to positions: 48, 49, 99, 108, 124, 149, 176, 229, 250, 257, 325, 356, 99+176+325, 49+99+176+325+356, 49+99+176+257+325+356, 99+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 49+99+124+176+257+325+356, 49+99+176+229+257+325+356, 229+250, 229+356, 49+99+176+229+250+257+325+356, 49+99+124+176+229+250+257+325+356, 49+99+108+124+176+229+250+257+325+356, 48+49+99+176+250+257+325+356, 49+99+176+250+325+257+356, and 48+257, (e.g., using the numbering according SEQ ID NO: 1) and/or (b) introducing into a parent pectate lyase (e.g., having SEQ ID NO:1 or SEQ ID NO: 2) one or more of the substitutions selected from the group consisting of: P48A, P48F, P48H, P48I, P48K, P48L, P48N, P48Q, P48R, P48S, P48T, P48W, P48Y, T49F, T49H, T49I, T49K, T49L, T49M, T49N, T49Q, T49R, T49V, T49W, T49Y, K99A, K99C, K99D, K99E, K99F, K99G, K99H, K99I, K99L, K99M, K99N, K99P, K99Q, K99S, K99T, K99V, K99W, K99Y, E108A, E108G, E108H, E108K, E108L, E108M, E108N, E108R, E108S, E108T, E108V, E108W, D124A, D124E, D124F, D124G, D124I, D124L, D124M, D124N, D124P, D124Q, D124R, D124S, D124T, D124V, D124W, S149K, S149L, S149R, S149W, S176A, S176C, S176D, S176E, S229I, S229K, S229L, S229M, S229Q, S229T, S229V, S229Y, I250A, I250G, I250L, I250M, I250N, I250S, I250T, K257A, K257C, K257D, K257H, K257I, K257L, K257M, K257Q, K257S, K257V, K257W, I325F, I325L, I325Y, Q356D, Q356E, Q356F, Q356G, Q356H, Q356I, Q356L, Q356N, Q356R, Q356T, Q356W, Q356Y, K99D+S176D+I325F, T49R+K99D+S176D+I325F+Q356F, T49R+K99D+S176D+K257L+I325F+Q356F, T49R+K99D+S176D+S229I+K257L+I325F+Q356F, K99D+S176D+I325F+Q356F, K99D+T49W+S176D+I325F+Q356F, K99D+D124W+S176D+I325F+Q356F, P48W+K99D+S176D+I325F+Q356F, K99D+E108N+S176D+I325F+Q356F, K99D+T49W+E108N+S176D+I325F+Q356F, P48W+S229I, S229I+K257L, S229I+I250N, S229I+Q356F, I250N+K257L, K257L+Q356F, P48W+I250N, P48W+Q356F, P48W+T49R+K99D+S176D+K257L+I325F+Q356F, P48W+T49W+K99D+S176D+K257L+I325F+Q356F, T49R+K99D+D124W+S176D+K257L+I325F+Q356F, T49R+K99D+S176D+S229I+K257L+I325F+Q356F, S229I+I250N, S229I+Q356F, T49R+K99D+D124W+S176D+S229I+I250N+K257L+I325F+Q356F, T49R+K99D+S176D+S229I+K257L+I325F+Q356F, T49R+K99D+S176D+S229I+I250N+K257L+I325F+Q356F, T49R+K99D+D124W+S176D+S229I+I250N+K257L+I325F+Q356F, T49R+K99D+E108N+D124W+S176D+S229I+I250N+K257L+I325F+Q356F, P48W+T49R+K99D+S176D+I250N+K257L+I325F+Q356F, T49R+K99D+S176D+I250N+I325F+K257L+Q356F, P48W+S229I, S229I+K257L, S229I+I250N, S229I+Q356F, P48W+K257L, I250N+K257L, K257L+Q356F, P48W+I250N, P48W+Q356F and I250N+Q356F, of the mature polypeptide of SEQ ID NO: 1, wherein the variant has pectate lyase activity; and (c) recovering the variant.

In a preferred embodiment the method comprising: (a) introducing into a parent pectate lyase (e.g., having SEQ ID NO:1) an alteration (or alterations) selected from the group consisting of:
P48W+S229I, S229I+K257L, S229I+I250N, S229I+Q356F, P48W+K257L, I250N+K257L, K257L+Q356F, P48W+I250N, P48W+Q356F, I250N+Q356F, K99D+S176D+I325F, T49R+K99D+S176D+I325F+Q356F, T49R+K99D+S176D+K257L+I325F+Q356F, T49R+K99D+S176D+S229I+K257L+I325F+Q356F, K99D+S176D+I325F+Q356F, K99D+T49W+S176D+I325F+Q356F, K99D+D124W+S176D+I325F+Q356F, P48W+K99D+S176D+I325F+Q356F, K99D+E108N+S176D+I325F+Q356F, K99D+T49W+E108N+S176D+I325F+Q356F, P48W+T49R+K99D+S176D+I250N+K257L+I325F+Q356F, T49R+K99D+S176D+S229I+I250N+K257L+I325F+Q356F, T49R+K99D+D124W+S176D+S229I+I250N+K257L+I325F+Q356F, T49R+K99D+E108N+D124W+S176D+S229I+I250N+K257L+I325F+Q356F, T49R+K99D+S176D+I250N+I325F+K257L+Q356F, P48W+T49R+K99D+S176D+K257L+I325F+Q356F, P48W+T49W+K99D+S176D+K257L+I325F+Q356F, T49R+K99D+D124W+S176D+K257L+I325F+Q356F, P48W+S229I, S229I+K257L, S229I+I250N, S229I+Q356F, P48W+K257L, I250N+K257L, K257L+Q356F, P48W+I250N, P48W+Q356F, I250N+Q356F, K99D+S176D+I325F, T49R+K99D+S176D+I325F+Q356F, T49R+K99D+S176D+K257L+I325F+Q356F, T49R+K99D+S176D+S229I+K257L+I325F+Q356F, K99D+S176D+I325F+Q356F, K99D+T49W+S176D+I325F+Q356F, K99D+D124W+S176D+I325F+Q356F, P48W+K99D+S176D+I325F+Q356F, K99D+E108N+S176D+I325F+Q356F, K99D+T49W+E108N+S176D+I325F+Q356F, P48W+T49R+K99D+S176D+I250N+K257L+I325F+Q356F, T49R+K99D+S176D+S229I+I250N+K257L+I325F+Q356F, T49R+K99D+D124W+S176D+S229I+I250N+K257L+I325F+Q356F, T49R+K99D+E108N+D124W+S176D+S229I+I250N+K257L+I325F+Q356F, T49R+K99D+S176D+I25 ON+I325F+K257L+Q356F, P48W+T49R+K99D+S176D+K257L+I325F+Q356F, P48W+T49W+K 99D+S176D+K257L+I325F+Q356F, T49R+K99D+D124W+S176D+K257L+I325F+Q356F andS229I+I250N+Q356F of the mature polypeptide of SEQ ID NO: 1, wherein the variant has pectate lyase activity; and (b) recovering the variant.

In a further aspect, the present invention also relates to methods for obtaining a variant having pectate lyase activity, comprising: (a) introducing into a parent pectate lyase (e.g., having SEQ ID NO:1 or SEQ ID NO: 2) a substitution at one or more (e.g., several) positions corresponding to positions 250, 176, 124, 108, 149, and 325, wherein numbering is according to the mature polypeptide of SEQ ID NO: 1, wherein the variant has pectate lyase activity; and (b) optionally, recovering the variant.

In some aspects (e.g., any of the aspects mentioned above), the method further comprises purifying the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention. Accordingly, in one aspect, the present invention relates to polynucleotides encoding a variant comprising an alteration at one or more positions selected from the group consisting of: 250, 176, 124, 325, 108, 149, 48, 49, 99, 229, 257, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+124+176+229+250+257+325+356, 49+99+176+229+250+257+325+356, 49+99+108+124+176+229+250+257+325+356, 48+49+99+176+250+257+325+356, 49+99+176+250+325+257+356, 48+257, and 229+250+356, wherein each position corresponds to a position of the amino acid sequence of the pectate lyase having the amino acid sequence of SEQ ID NO:1, and wherein the variant has at least 65%, but less than 100% identity to the amino acid sequence of SEQ ID NO:1.

In another aspect, the present invention relates to polynucleotides encoding a variant comprising an alteration at one or more positions selected from the group consisting of positions 250, 176, 124, 108, 149, and 325, wherein numbering is according to SEQ ID NO: 1, and wherein the alteration(s) are independently:

(i) an insertion of an amino acid downstream of the amino acid which occupides the position;

(ii) a deletion of the amino acid which occupies the position; or (iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences. Accordingly, in one aspect, the present invention relates to nucleic acid constructs comprising a polynucleotide encoding a variant comprising an alteration at one or more positions selected from the group consisting of: 250, 176, 124, 325, 108, 149, 48, 49, 99, 229, 257, 356, 99+176+325, 49+99+176+325+356, 49+99+176+257+325+ 356, 49+99+176+229+257+325+356, 99+176+325+356, 99+49+176+325+356, 99+124+176+325+356, 48+99+176+

325+356, 99+108+176+325+356, 99+49+108+176+325+ 356, 48+229, 229+257, 229+250, 229+356, 250+257, 257+ 356, 48+250, 48+356, 250+356, 48+49+99+176+257+325+ 356, 48+49+99+176+257+325+356, 49+99+124+176+257+ 325+356, 49+99+124+176+229+250+257+325+356, 49+99+176+229+250+257+325+356, 49+99+108+124+ 176+229+250+257+325+356, 48+49+99+176+250+257+ 325+356, 49+99+176+250+325+257+356, 48+257, and 229+250+356, wherein each position corresponds to a position of the amino acid sequence of the pectate lyase having the amino acid sequence of SEQ ID NO:1, and wherein the variant has at least 65%, but less than 100% identity to the amino acid sequence of SEQ ID NO:1, which is operably linked to one or more control sequences that direct the expression of the coding sequence in a suitable host cell under conditions compatible with the control sequences.

In another aspect, the present invention relates to nucleic acid constructs comprising a polynucleotide encoding a variant comprising an alteration at one or more positions selected from the group consisting of positions 250, 176, 124, 108, 149, and 325, wherein numbering is according to SEQ ID NO: 1, and wherein the alteration(s) are independently:

(i) an insertion of an amino acid downstream of the amino acid which occupides the position;
(ii) a deletion of the amino acid which occupies the position; or
(iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1, which is operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the Bacillus amyloliquefaciens alpha-amylase gene (amyQ), Bacillus licheniformis alpha-amylase gene (amyL), Bacillus licheniformis penicillinase gene (penP), Bacillus stearothermophilus maltogenic amylase gene (amyM), Bacillus subtilis levansucrase gene (sacB), Bacillus subtilis xylA and xylB genes, Bacillus thuringiensis cryIIIA gene (Agaisse and Lereclus, 1994, Molecular Microbiology 13: 97-107), E. coli lac operon, E. coli trc promoter (Egon et al., 1988, Gene 69: 301-315), Streptomyces coelicolor agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for Aspergillus nidulans acetamidase, Aspergillus niger neutral alpha-amylase, Aspergillus niger acid stable alpha-amylase, Aspergillus niger or Aspergillus awamori glucoamylase (glaA), Aspergillus oryzae TAKA amylase, Aspergillus oryzae alkaline protease, Aspergillus oryzae triose phosphate isomerase, Fusarium oxysporum trypsin-like protease (WO 96/00787), Fusarium venenatum amyloglucosidase (WO 00/56900), Fusarium venenatum Daria (WO 00/56900), Fusarium venenatum Quinn (WO 00/56900), Rhizomucor miehei lipase, Rhizomucor miehei aspartic proteinase, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase IV, Trichoderma reesei endoglucanase V, Trichoderma reesei xylanase I, Trichoderma reesei xylanase II, Trichoderma reesei beta-xylosidase, as well as the NA2-tpi promoter (a modified promoter from an Aspergillus neutral alpha-amylase gene in which the untranslated leader has been replaced by an untranslated leader from an Aspergillus triose phosphate isomerase gene; non-limiting examples include modified promoters from an Aspergillus niger neutral alpha-amylase gene in which the untranslated leader has been replaced by an untranslated leader from an Aspergillus nidulans or Aspergillus oryzae triose phosphate isomerase gene); and mutant, truncated, and hybrid promoters thereof.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for Bacillus clausii alkaline protease (aprH), Bacillus licheniformis alpha-amylase (amyL), and Escherichia coli ribosomal RNA (rrnB).

Preferred terminators for filamentous fungal host cells are obtained from the genes for Aspergillus nidulans anthranilate synthase, Aspergillus niger glucoamylase, Aspergillus niger alpha-glucosidase, Aspergillus oryzae TAKA amylase, and Fusarium oxysporum trypsin-like protease.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. Accordingly, in one aspect the present invention relates to recombinant expression vectors comprising a polynucleotide encoding a variant comprising an alteration at one or more positions selected from the group consisting of: 250, 176, 124, 325, 108, 149, 48, 49, 99, 229, 257, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+124+176+229+250+257+325+356, 49+99+176+229+250+257+325+356, 49+99+108+124+176+229+250+257+325+356, 48+49+99+176+250+257+325+356, 49+99+176+250+325+257+356, 48+257, and 229+250+356, wherein each position corresponds to a position of the amino acid sequence of the pectate lyase having the amino acid sequence of SEQ ID NO:1, and wherein the variant has at least 65%, but less than 100% identity to the amino acid sequence of SEQ ID NO:1, a promoter, and transcriptional and translational stop signals.

In another aspect, the present invention relates to recombinant expression vectors comprising a polynucleotide encoding a variant comprising an alteration at one or more positions selected from the group consisting of positions 250, 176, 124, 108, 149, and 325, wherein numbering is according to SEQ ID NO: 1, and wherein the alteration(s) are independently:
 (i) an insertion of an amino acid downstream of the amino acid which occupides the position;
 (ii) a deletion of the amino acid which occupies the position; or
 (iii) a substitution of the amino acid which occupies the position with a different amino acid,
and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1, a promoter, and transcriptional and translational stop signals.

The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. Accordingly, in one aspect, the present invention relates to recombinant host cells, comprising a polynucleotide encoding a variant of the present invention operably linked to one or more control sequences that direct the production of a variant comprising an alteration at one or more positions selected from the group consisting of: 250, 176, 124, 325, 108, 149, 48, 49, 99, 229, 257, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+124+176+229+250+257+325+356, 49+99+176+229+250+257+325+356, 49+99+108+124+176+229+250+257+325+356, 48+49+99+176+250+257+325+356, 49+99+176+250+325+257+356, 48+257, and 229+250+356, wherein each position corresponds to a position of the amino acid sequence of the pectate lyase having the amino acid sequence of SEQ ID NO:1, and wherein the variant has at least 65%, but less than 100% identity to the amino acid sequence of SEQ ID NO:1.

In another aspect, the present invention relates to recombinant host cells, comprising a polynucleotide encoding a variant comprising an alteration at one or more positions selected from the group consisting of positions 250, 176, 124, 108, 149, and 325, wherein numbering is according to SEQ ID NO: 1, and wherein the alteration(s) are independently:
  (i) an insertion of an amino acid downstream of the amino acid which occupides the position;
  (ii) a deletion of the amino acid which occupies the position; or
  (iii) a substitution of the amino acid which occupies the position with a different amino acid,
  and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1.

A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausfi*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell, including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulaturn, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant. Thus, in one aspect, the present invention relates to methods of producing a variant, comprising: (a) cultivating a host cell expressing a variant comprising an alteration at one or more positions selected from the group consisting of: 250, 176, 124, 325, 108, 149, 48, 49, 99, 229, 257, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+124+176+229+250+257+325+356, 49+99+176+229+250+257+325+356, 49+99+108+124+176+229+250+257+325+356, 48+49+99+176+250+257+325+356, 49+99+176+250+325+257+356, 48+257, and 229+250+356, wherein each position corresponds to a position of the amino acid sequence of the pectate lyase having the amino acid sequence of SEQ ID NO:1 under conditions suitable for expression of the variant; and (b) optionally, recovering the variant.

In another aspect, the present invention relates to methods of producing a variant, comprising: (a) cultivating a host cell expressing a variant comprising an alteration at one or more positions selected from the group consisting of positions 250, 176, 124, 108, 149, and 325, wherein numbering is according to SEQ ID NO: 1, and wherein the alteration(s) are independently:

(i) an insertion of an amino acid downstream of the amino acid which occupies the position;

(ii) a deletion of the amino acid which occupies the position; or (iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1 under conditions suitable for expression of the variant; and (b) optionally, recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Uses of the Variants

Use in the Detergent Industry

In further aspects, the present invention relates to a detergent composition comprising the pectate lyase variant or pectate lyase variant preparation of the invention. Accordingly, in one aspect, the present invention relates to a detergent composition comprising the pectate lyase variant comprising an alteration at one or more positions selected from the group consisting of: 250, 176, 124, 325, 108, 149, 48, 49, 99, 229, 257, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+124+176+229+250+257+325+356, 49+99+176+229+250+257+325+356, 49+99+108+124+176+229+250+257+325+356, 48+49+99+176+250+257+325+356, 49+99+176+250+325+257+356, 48+257, and 229+250+356, wherein each position corresponds to a position of the amino acid sequence of the pectate lyase having the amino acid sequence of SEQ ID NO:1, or pectate lyase variant preparation comprising a variant comprising an alteration at one or more positions selected from the group consisting of: 250, 176, 124, 325, 108, 149, 48, 49, 99, 229, 257, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+124+176+229+250+257+325+356, 49+99+176+229+250+257+325+356, 49+99+108+124+176+229+250+257+325+356, 48+49+99+176+250+257+325+356, 49+99+176+250+325+257+356, 48+257, and 229+250+356, wherein each position corresponds to a position of the amino acid sequence of the pectate lyase having the amino acid sequence of SEQ ID NO:1.

In another aspect, the present invention relates to a detergent composition comprising the pectate lyase variant comprising an alteration at one or more positions selected from the group consisting of positions 250, 176, 124, 108, 149, and 325, wherein numbering is according to SEQ ID NO: 1, and wherein the alteration(s) are independently:

(i) an insertion of an amino acid downstream of the amino acid which occupides the position;

(ii) a deletion of the amino acid which occupies the position; or (iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1, or pectate lyase variant preparation comprising a variant comprising an alteration at one or more positions selected from the group consisting of positions 250, 176, 124, 108, 149, and 325, wherein numbering is according to SEQ ID NO: 1, and wherein the alteration(s) are independently:

(i) an insertion of an amino acid downstream of the amino acid which occupides the position;

(ii) a deletion of the amino acid which occupies the position; or (iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1.

The detergent compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

In one embodiment of the present invention, the variant of the present invention may be added to a detergent composition in an amount corresponding to 0.001-200 mg of protein, such as 0.005-100 mg of protein, preferably 0.01-50 mg of protein, more preferably 0.05-20 mg of protein, even more preferably 0.1-10 mg of protein per liter of wash liquor. In one embodiment, the invention is directed to detergent compositions comprising a variant of the present invention in combination with one or more additional cleaning composition components. The choice of additional components is within the skill of the artisan and includes conventional ingredients, including the exemplary non-limiting components set forth below.

The choice of components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

In one embodiment, the invention is directed to automatic dish wash (ADW) compositions comprising a variant of the present invention in combination with one or more additional ADW composition components. The choice of additional components is within the skill of the artisan and includes conventional ingredients, including the exemplary non-limiting components set forth below.

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually comprise from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually comprise from about from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyl-dimethyl-ammonium, alkyl quaternary ammonium compounds, alkoxylated quaternary ammonium (AQA) compounds, ester quats, and combinations thereof.

When included therein the detergent will usually comprise from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

The detergent may include a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

The detergent may include a zwitterionic surfactant. Non-limiting examples of zwitterionic surfactants include betaines such as alkyldimethylbetaines, sulfobetaines, and combinations thereof.

The detergent composition may comprise one or more surfactants hydrotrope. A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined mesophases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may comprise 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

The detergent composition may comprise about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry and/or ADW detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-01), triethanolamine (TEA, also known as 2,2',2"-nitrilotriethan-1-ol), and (carboxymethyl)inulin (CMI), and combinations thereof.

The detergent composition may also comprise 0-50% by weight, such as about 5% to about 30%, of a detergent co-builder. The detergent composition may include include a co-builder alone, or in combination with a builder, for example a zeolite builder. Non-limiting examples of co-builders include homopolymers of polyacrylates or copolymers thereof, such as poly(acrylic acid) (PAA) or copoly (acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylene-triamine-pentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MI DA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylene-triamine penta (methylenephosphonic acid) (DTPMP), aminotris (methylenephosphonic acid) (ATMP), and combinations and salts thereof. Further exemplary builders and/or co-builders are described in, e.g., WO 09/102854, U.S. Pat. No. 5,977,053 The detergent may comprise 0-30% by weight, such as about 1% to about 20%, of a bleaching system. Any bleaching system known in the art for use in laundry and/or ADW detergents may be utilized. Suitable bleaching system components include bleaching catalysts, photobleaches, bleach activators, sources of hydrogen peroxide such as sodium percarbonate, sodium perborates and hydrogen peroxide—urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy] benzene-1-sulfonate (ISONOBS), 4-(dodecanoyloxy) benzene-1-sulfonate (LOBS), 4-(decanoyloxy)benzene-1-sulfonate, 4-(decanoyloxy) benzoate (DOBS or DOBA), 4-(nonanoyloxy)benzene-1-sulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also corrprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

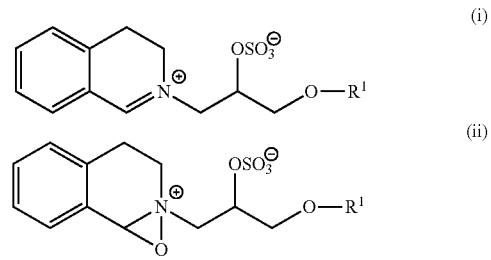

(iii) and mixtures thereof;

wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Preferably the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

The detergent composition may comprise 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly (vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

The detergent compositions of the present invention may also comprise fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

The detergent additive as well as the detergent composition may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes NS) Carezyme Premium™ (Novozymes NS), Celluclean™ (Novozymes NS), Celluclean Classic™ (Novozymes NS), Cellusoft™ (Novozymes NS), Whitezyme™ (Novozymes NS), Clazinase™, and Puradax HA™ (Genencor International Inc.), and KAC-500(B)™ (Kao Corporation).

Suitable mannanases include those of bacterial or fungal origin. Chemically or genetically modified mutants are included. The mannanase may be an alkaline mannanase of Family 5 or 26. It may be a wild-type from Bacillus or Humicola, particularly B. agaradhaerens, B. licheniformis, B. halodurans, B. clausii, or H. insolens. Suitable mannanases are described in WO 1999/064619. A commercially available mannanase is Mannaway (Novozymes NS).

Suitable peroxidases/oxidases include those of plant, bacterial or fungal origin. Chemically modified or protein engineered mutants are included. Examples of useful peroxidases include peroxidases from Coprinus, e.g., from C. cinereus, and variants thereof as those described in WO 93/24618, WO 95/10602, and WO 98/15257. Commercially available peroxidases include Guardzyme™ (Novozymes NS).

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from Bacillus such as Bacillus lentus, B. alkalophilus, B. subtilis, B. amyloliquefaciens, Bacillus pumilus and Bacillus gibsonii described in; U.S. Pat. No. 7,262,042 and WO09/021867, and subtilisin lentus, subtilisin Novo, subtilisin Carlsberg, Bacillus licheniformis, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the Fusarium protease described in WO89/06270, WO94/25583 and WO05/040372, and the chymotrypsin proteases derived from Cellumonas described in WO05/052161 and WO05/052146.

A further preferred protease is the alkaline protease from Bacillus lentus DSM 5483, as described for example in WO95/23221, and variants thereof which are described in WO92/21760, WO95/23221, EP1921147 and EP1921148.

Suitable lipases and cutinases include those of bacterial or fungal origin. Chemically modified or protein engineered mutant enzymes are included. Examples include lipase from

*Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from Thermobifida fusca (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Preferred commercial lipase products include include Lipolase™, Lipex™; Lipolex™ and Lipoclean™ (Novozymes NS), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Suitable amylases which can be used together with the variant of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467.

Commercially available amylases are DURAMYL™, LIQUEZYME™, TERMAMYL™, NATALASE™, Everest™, FUNGAMYL™ and BAN™, Amplify™, Amplify Prime™, Stainzyme™, Stainzyme Plus® (Novozymes NS), Preferenz S100, Preferenz S110, Preferenz S1000, Excellenz S110, Excellenz S1000, Excellenz S2000, RAPIDASE™ and PURASTAR™ (from Genencor International Inc./DuPont).

The composition may comprise peroxidase and/or oxidases.

A peroxidase is a peroxidase enzyme comprised by the enzyme classification EC 1.11.1.7.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

An oxidase according to the invention include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), ora bilirubin oxidase (EC 1.3.3.5).

Preferred laccase enzymes are enzymes of microbial origin. The enzymes may be derived from plants, bacteria or fungi (including filamentous fungi and yeasts).

A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are polyethyleneglycol (PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Any detergent components known in the art for use in laundry and/or ADW detergents may also be utilized. Such optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. The choice of such ingredients is well within the skill of the artisan.

The detergent compositions of the present invention can also comprise dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

The detergent compositions of the present invention may also comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

The detergent compositions of the present invention may also comprise additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bis-phenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.
Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

The detergent compositions of the present invention may also comprise one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose derivitaives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

The detergent compositions of the present invention may also comprise one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

The detergent compositions of the present invention may also comprise one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable ingredients include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

The detergent composition comprising a variant of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%.

Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically comprising at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may comprise from 0-30% organic solvent. A liquid or gel detergent may be non-aqueous.

The variant of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may comprise one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also comprise complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, a variant of the invention, optionally one or more additional enzymes, a protease inhibitor, and a salt of a monovalent cation and an organic anion may be prepared and the mixture is then plodded. The variant and optional additional enzymes may be added at the same time as the protease inhibitor for example in liquid form. Besides the mixing step and the plodding step, the process may further comprise the steps of milling, extruding, cutting, stamping, cooling and/or wrapping.

The enzyme of the invention may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component.

WO 2013/188331 also relates to a method of treating and/or cleaning a surface, preferably a fabric surface comprising the steps of (i) contacting said surface with the detergent composition as claimed and described herein in an aqueous wash liquor, (ii) rinsing and/or drying the surface.

The multi-enzyme co-granule may comprise an enzyme of the invention and (a) one or more enzymes selected from the group consisting of lipases, cleaning cellulases, xyloglucanases, perhydrolases, peroxidases, lipoxygenases, laccases and mixtures thereof; and (b) one or more enzymes selected from the group consisting of hemicellulases, proteases, care cellulases, cellobiose dehydrogenases, xylanases, phospholipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

Use in the Textile and Cellulosic Fiber Processing Industries

The pectate lyase variant of the present invention can be used in combination with other carbohydrate-degrading enzymes (for instance hemicellulases, such as arabinanase, xyloglucanase, mannanase and pectinase) for biopreparation of fibers or for cleaning of fibers in combination with detergents. Accordingly, in one aspect, the present invention relates to the use of a variant comprising an alteration at one or more positions selected from the group consisting of: 250, 176, 124, 325, 108, 149, 48, 49, 99, 229, 257, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+124+176+229+250+257+325+356, 49+99+176+229+250+257+325+356, 49+99+108+124+176+229+250+257+325+356, 48+49+99+176+250+257+325+356, 49+99+176+250+325+257+356, 48+257, and 229+250+356, wherein each position corresponds to a position of the amino acid sequence of the pectate lyase having the amino acid sequence of SEQ ID NO:1, and wherein the variant has at least 65%, but less than 100% identity to the amino acid sequence of SEQ ID NO:1 in combination with other carbohydrate-degrading enzymes, such as hemicellulases, more particularly, arabinananse, xyloglucanase, mannanase and pectinase, for biopreparation of fibers or for cleaning of fibers in combination with detergents.

In another aspect, the present invention relates to the use of a variant comprising an alteration at one or more positions selected from the group consisting of positions 250, 176, 124, 108, 149, and 325, wherein numbering is according to SEQ ID NO: 1, and wherein the alteration(s) are independently:

(i) an insertion of an amino acid downstream of the amino acid which occupides the position;

(ii) a deletion of the amino acid which occupies the position; or (iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1 in combination with other carbohydrate-degrading enzymes, such as hemicellulases, more particularly, arabinananse, xyloglucanase, mannanase and pectinase, for biopreparation of fibers or for cleaning of fibers in combination with detergents.

Cotton fibers consist of a primary cell wall layer containing pectin and a secondary layer containing mainly cellulose. Under cotton preparation or cotton refining part of the primary cell wall will be removed. The variant of the present invention may thus be applied either help during cotton refining for removal of the primary cell wall, or during cleaning of the cotton for remove residual pectic substances and prevent graying of the textile.

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The variants of the present invention is useful in the cellulosic fiber processing industry for the pre-treatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in preparation are a. desizing (for woven goods) using polymeric size like e.g. starch, CMC or PVA is added before weaving in order to increase the warp speed; This material must be removed before further processing.

b. scouring, the aim of which is to remove non-cellulosic material from the cotton fiber, especially the cuticle (mainly consisting of waxes) and primary cell wall (mainly consisting of pectin, protein and xyloglucan). A proper wax removal is necessary for obtaining a high wettability, being a measure for obtaining a good dyeing. Removal of the primary cell wall—especially the pectins—improves wax removal and ensures a more even dyeing. Further this improves the whiteness in the bleaching process. The main chemical used in scouring is sodium hydroxide in high concentrations, up to 70 g/kg cotton and at high temperatures, 80-95° C.; and c. bleaching; normally the scouring is followed by a bleach using hydrogen peroxide as the oxidizing agent in order to obtain either a fully bleached (white) fabric or to ensure a clean shade of the dye.

A one step combined scour/bleach process is also used by the industry. Although the processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8-15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period, which, in the case of cold pad-batch, might be one or more days.

Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative processes are often used. The most common sizing agent for cotton fabric is based upon starch. Therefore most often, woven cotton fabrics are desized by a combination of hot water, the enzyme alfa-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath which generally ranges from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following processes: scouring and bleaching.

The scouring process removes much of the non-cellulosic compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80-100° C., employing strongly alkaline solutions, pH 13-14, of the scouring agent. Due to the non-specific nature of chemical processes not only are the impurities but the cellulose itself is attacked, leading to damages in strength or other desirable fabric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

The scouring step can be carried out using the pectate lyase variant of the present invention a temperature of about 50-80° C. and a pH of about 7-11, thus substituting or supplementing the highly causticizing agents. An optimized enzymatic process ensures a high pectin removal and full wettability.

Use for Degradation or Modification of Plant Material

The variant according to the invention is preferably used as an agent for degradation or modification of plant cell walls or any pectin-containing material originating from plant cell walls due to the high plant cell wall degrading activity of the pectate lyase variant of the invention. Thus, in one aspect of the present invention, the variant comprising an alteration at one or more positions selected from the group consisting of: 250, 176, 124, 325, 108, 149, 48, 49, 99, 229, 257, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+124+176+229+250+257+325+356, 49+99+108+124+176+229+250+257+325+356, 48+49+99+176+250+257+325+356, 49+99+176+250+ 325+257+356, 48+257, and 229+250+356, wherein each position corresponds to a position of the amino acid sequence of the pectate lyase having the amino acid sequence of SEQ ID NO:1, and wherein the variant has at least 65%, but less than 100% identity to the amino acid sequence of SEQ ID NO:1 is used as an agent for degradation or modification of plant cell walls or any pectin-containing material originating from plant cell walls due to the high plant cell wall degrading activity of the pectate lyase variant comprising an alteration at one or more positions selected from the group consisting of: 250, 176, 124, 325, 108, 149, 48, 49, 99, 229, 257, 356, 99+176+325, 49+99+176+325+356, 49+99+176+257+325+356, 49+99+ 176+229+257+325+356, 99+176+325+356, 99+49+176+ 325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+ 325+356, 49+99+124+176+229+250+257+325+356, 49+99+176+229+250+257+325+356, 49+99+108+124+ 176+229+250+257+325+356, 48+49+99+176+250+257+ 325+356, 49+99+176+250+325+257+356, 48+257, and 229+250+356, wherein each position corresponds to a position of the amino acid sequence of the pectate lyase having the amino acid sequence of SEQ ID NO:1, and wherein the variant has at least 65%, but less than 100% identity to the amino acid sequence of SEQ ID NO:1.

In another aspect of the present invention, the variant comprising an alteration at one or more positions selected from the group consisting of positions 250, 176, 124, 108, 149, and 325, wherein numbering is according to SEQ ID NO: 1, and wherein the alteration(s) are independently:
 (i) an insertion of an amino acid downstream of the amino acid which occupides the position;
 (ii) a deletion of the amino acid which occupies the position; or
 (iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1 is used as an agent for degradation or modification of plant cell walls or any pectin-containing material originating from plant cell walls due to the high plant cell wall degrading activity of the pectate lyase variant comprising an alteration at one or more positions selected from the group consisting of positions 250, 176, 124, 108, 149, and 325, wherein numbering is according to SEQ ID NO: 1, and wherein the alteration(s) are independently:
 (i) an insertion of an amino acid downstream of the amino acid which occupides the position;
 (ii) a deletion of the amino acid which occupies the position; or
 (iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1.

The pectate lyase variant of the present invention may be used alone or together with other enzymes like glucanases, pectinases and/or hemicellulases to improve the extraction of oil from oil-rich plant material, like soy-bean oil from soy-beans, olive-oil from olives or rapeseed-oil from rapeseed or sunflower oil from sunflower.

The pectate lyase variant of the present invention may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions. The separation process may be performed by use of methods known in the art.

The pectate lyase variant of the invention may also be used in the preparation of fruit or vegetable juice in order to increase yield, and in the enzymatic hydrolysis of various plant cell wall-derived materials or waste materials, e.g. from wine or juice production, or agricultural residues such as vegetable hulls, bean hulls, sugar beet pulp, olive pulp, potato pulp, and the like.

The plant material may be degraded in order to improve different kinds of processing, facilitate purification or extraction of other component than the galactans like purification of pectins from citrus, improve the feed value, decrease the water binding capacity, improve the degradability in waste water plants, improve the conversion of plant material to ensilage, etc.

By means of an variant of the invention it is possible to regulate the consistency and appearance of processed fruit or vegetables. The consistency and appearance has been shown to be a product of the actual combination of enzymes used for processing, i.e. the specificity of the enzymes with which the pectate lyase variant of the invention is combined. Examples include the production of clear juice e.g. from apples, pears or berries; cloud stable juice e.g. from apples, pears, berries, citrus or tomatoes; and purees e.g. from carrots and tomatoes.

The pectate lyase variant of the invention may be used in modifying the viscosity of plant cell wall derived material. For instance, the pectate lyase variant may be used to reduce the viscosity of feed containing galactan and to promote processing of viscous galactan containing material. The viscosity reduction may be obtained by treating the galactan containing plant material with a variant of the invention under suitable conditions for full or partial degradation of the galactan containing material The pectate lyase variant can be used e.g. in combination with other enzymes for the removal of pectic substances from plant fibres. This removal is essential e.g. in the production of textile fibres or other cellulosic materials. For this purpose plant fibre material is treated with a suitable amount of the pectate lyase of the invention under suitable conditions for obtaining full or partial degradation of pectic substances associated with the plant fibre material.

Use as Animal Feed Additive

Pectate lyase variants of the present invention may be used for modification of animal feed and may exert their effect either in vitro (by modifying components of the feed) or in vivo. Accordingly, the pectate lyase variants comprising an alteration at one or more positions selected from the group consisting of: 250, 176, 124, 325, 108, 149, 48, 49, 99, 229, 257, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+124+176+229+250+257+325+356, 49+99+176+229+250+257+325+356, 49+99+108+124+176+229+250+257+325+356, 48+49+99+176+250+257+325+356, 49+99+176+250+325+257+356, 48+257, and 229+250+356, wherein each position corresponds to a position of the amino acid sequence of the pectate lyase having the amino acid sequence of SEQ ID NO:1, and wherein the variant has at least 65%, but less than 100% identity to the amino acid sequence of SEQ ID NO:1 may be used for modification of animal feed and may exert their effect either in vitro (by modifying components of the feed) or in vivo.

In another aspect, the pectate lyase variants comprising an alteration at one or more positions selected from the group consisting of positions 250, 176, 124, 108, 149, and 325, wherein numbering is according to SEQ ID NO: 1, and wherein the alteration(s) are independently:

(i) an insertion of an amino acid downstream of the amino acid which occupides the position;

(ii) a deletion of the amino acid which occupies the position; or (iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1 may be used for modification of animal feed and may exert their effect either in vitro (by modifying components of the feed) or in vivo.

The pectate lyase variant is particularly suited for addition to animal feed compositions containing high amounts of arabinogalactans or galactans, e.g. feed containing plant material from soy bean, rape seed, lupin etc. When added to the feed the pectate lyase variant significantly improves the in vivo break-down of plant cell wall material, whereby a better utilization of the plant nutrients by the animal is achieved. Thereby, the growth rate and/or feed conversion ratio (i.e. the weight of ingested feed relative to weight gain) of the animal is improved. For example the indigestible galactan is degraded by pectate lyase, e.g. in combination with beta-galactosidase, to galactose or galactooligomers which are digestible by the animal and thus contributes to the available energy of the feed. Also, by the degradation of galactan the pectate lyase may improve the digestibility and uptake of non-carbohydrate feed constituents such as protein, fat and minerals.

Use in Wine and Juice Processing

The variant of the invention may be used for de-pectinization and viscosity reduction in vegetable or fruit juice, especially in apple or pear juice. Accordingly, the pectate lyase variant comprising an alteration at one or more positions selected from the group consisting of: 250, 176, 124, 325, 108, 149, 48, 49, 99, 229, 257, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+124+176+229+250+257+325+356, 49+99+176+229+250+257+325+356, 49+99+108+124+176+229+250+257+325+356, 48+49+99+176+250+257+325+356, 49+99+176+250+325+257+356, 48+257, and 229+250+356, wherein each position corresponds to a position of the amino acid sequence of the pectate lyase having the amino acid sequence of SEQ ID NO:1, and wherein the variant has at least 65%, but less than 100% identity to the amino acid sequence of SEQ ID NO:1 may be used for de-pectinization and optionally, viscosity reduction in vegetable or fruit juice, especially in apple or pear juice.

In another aspect, the pectate lyase variant comprising an alteration at one or more positions selected from the group consisting of positions 250, 176, 124, 108, 149, and 325, wherein numbering is according to SEQ ID NO: 1, and wherein the alteration(s) are independently:

(i) an insertion of an amino acid downstream of the amino acid which occupides the position;

(ii) a deletion of the amino acid which occupies the position; or (iii) a substitution of the amino acid which occupies the position with a different amino acid, and wherein each position corresponds to a position of the amino acid sequence of the pectate lyase having the amino acid sequence of SEQ ID NO: 1, and wherein the variant pectate lyase has at least 75% identity to the amino acid sequence of SEQ ID NO: 1 may be used for de-pectinization and optionally, viscosity reduction in vegetable or fruit juice, especially in apple or pear juice.

This may be accomplished by treating the fruit or vegetable juice with a variant of the invention in an amount effective for degrading pectin-containing material contained in the fruit or vegetable juice.

The variant may be used in the treatment of mash from fruits and vegetables in order to improve the extractability or degradability of the mash. For instance, the variant may be used in the treatment of mash from apples and pears for juice production, and in the mash treatment of grapes for wine production.

The Invention is Further Defined in the Following Paragraphs:

1. A pectate lyase variant, wherein said variant has pectate lyase activity (e.g., EC 4.2.2.2) and comprises an alteration(s) (e.g., a substitution(s), insertion(s) or deletion(s)) at one or more positions selected from the group consisting of positions (e.g., combinations of positions): 48, 49, 99, 108, 124, 149, 176, 229, 250, 257, 325, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+176+229+257+325+356, 229+250, 229+356, 49+99+124+176+229+250+257+325+356, 49+99+176+229+257+325+356, 49+99+176+229+250+257+325+356, 49+99+124+176+229+250+257+325+356, 49+99+108+124+176+229+250+257+325+356, 48+49+99+176+250+257+325+356, 49+99+176+250+325+257+356, 48+229, 229+257, 229+250, 229+356, 48+257, 250+257, 257+356, 48+250, 48+356, 250+356, 229+250+356, wherein each position corresponds to a position of the amino acid sequence of the pectate lyase having the amino acid sequence of SEQ ID NO:1 (e.g., using the numbering of SEQ ID NO: 1), and wherein the variant has at least 65%, e.g., at least 70%, at least 75%, at least 80%, at least 85%, at least 90%, at least 95%, at least 96%, at least 97%, at least 98%, or at least 99%, but less than 100% identity to the amino acid sequence of SEQ ID NO:1 or SEQ ID NO: 2.

2. The variant of paragraph 1, which is a variant of a parent pectate lyase selected from the group consisting of:

a) a polypeptide having at least 60%, e.g., at least 65%, at least 70%, at least 75%, at least 80%, at least 85%, at least 90%, at least 95%, at least 96%, at least 97%, at least 98%, at least 99% or 100%, sequence identity to the amino acid sequence of SEQ ID NO:1 or SEQ ID NO: 2;

b) a polypeptide encoded by a polynucleotide that hybridizes under low, medium, or high stringency conditions with (i) sequence encoding the polypeptide of SEQ ID NO: 1 or SEQ ID NO: 2, or (ii) the full-length complement of (i);

c) a polypeptide encoded by a polynucleotide having at least 75%, e.g., at least 80%, at least 85%, at least 90%, at least 95%, at least 96%, at least 97%, at least 98%, or at least 99%, identity to sequence encoding the polypeptide of SEQ ID NO: 1 or SEQ ID NO: 2; and d) a fragment of the polypeptide of SEQ ID NO: 1 or SEQ ID NO: 2, which has pectate lyase activity.

3. The variant of paragraph 2, wherein the parent pectate lyase comprises or consists of the amino acid sequence of SEQ ID NO:1 or SEQ ID NO: 2.

4. The variant according to any of preceding paragraphs, wherein said variant has at least 65%, e.g., at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% identity to the amino acid sequence of SEQ ID NO:1 or SEQ ID NO: 2.

5. The variant according to any preceding paragraphs, wherein said alteration is a substitution.

6. The variant of paragraph 5, wherein said substitution is with a positively charged amino acid, preferably said positively charged amino acid is lysine or arginine.

7. The variant according to any of preceding paragraphs, wherein the variant comprises one or more substitutions selected from the group consisting of substitutions (e.g., combinations of substitutions): P48A, P48F, P48H, P48I, P48K, P48L, P48N, P48Q, P48R, P48S, P48T, P48W, P48Y, T49F, T49H, T49I, T49K, T49L, T49M, T49N, T49Q, T49R, T49V, T49W, T49Y, K99A, K99C, K99D, K99E, K99F, K99G, K99H, K99I, K99L, K99M, K99N, K99P, K99Q, K99S, K99T, K99V, K99W, K99Y, E108A, E108G, E108H, E108K, E108L, E108M, E108N, E108R, E108S, E108T, E108V, E108W, D124A, D124E, D124F, D124G, D124I, D124L, D124M, D124N, D124P, D124Q, D124R, D124S, D124T, D124V, D124W, S149K, S149L, S149R, S149W, S176A, S176C, S176D, S176E, S229I, S229K, S229L, S229M, S229Q, S229T, S229V, S229Y, I250A, I250G, I250L, I250M, I250N, I250S, I250T, K257A, K257C, K257D, K257H, K257I, K257L, K257M, K257Q, K257S, K257V, K257W, I325F, I325L, I325Y, Q356D, Q356E, Q356F, Q356G, Q356H, Q356I, Q356L, Q356N, Q356R, Q356T, Q356W, Q356Y, K99D+S176D+I325F, T49R+K99D+S176D+I325F+Q356F, T49R+K99D+S176D+K257L+I325F+Q356F, T49R+K99D+S176D+S229I+K257L+I325F+Q356F, K99D+S176D+I325F+Q356F, K99D+T49W+S176D+I325F+Q356F, K99D+D124W+S176D+I325F+Q356F, P48W+K99D+S176D+I325F+Q356F, K99D+E108N+S176D+I325F+Q356F, K99D+T49W+E108N+S176D+I325F+Q356F, P48W+S229I, S229I+K257L, S229I+I250N, S229I+Q356F, I250N+K257L, K257L+Q356F, P48W+I250N, P48W+Q356F, I250N+Q356F, P48W+ T49R+K99D+S176D+K257L+I325F+Q356F, P48W+ T49W+K99D+S176D+K257L+I325F+Q356F, T49R+ K99D+D124W+S176D+K257L+I325F+Q356F, T49R+ K99D+S176D+S229I+K257L+I325F+Q356F, S229I+ I250N, S229I+Q356F, T49R+K99D+D124W+S176D+ S229I+I250N+K257L+I325F+Q356F, T49R+K99D+ S176D+S229I+K257L+I325F+Q356F, T49R+K99D+ S176D+S229I+I250N+K257L+I325F+Q356F, T49R+ K99D+D124W+S176D+S229I+I250N+K257L+I325F+ Q356F, T49R+K99D+E108N+D124W+S176D+S229I+ I250N+K257L+I325F+Q356F, P48W+T49R+K99D+ S176D+I250N+K257L+I325F+Q356F, T49R+K99D+ S176D+I250N+I325F+K257L+Q356F, P48W+S229I, S229I+K257L, S229I+I250N, S229I+Q356F, P48W+ K257L, I250N+K257L, K257L+Q356F, P48W+I250N, P48W+Q356F and I250N+Q356F and S229I+I250N+ Q356F.

8. The variant according to any of preceding paragraphs, wherein the variant is selected from the group consisting of:
a) a polypeptide having at least 75%, e.g., at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, at least 99.1%, at least 99.2%, at least 99.3%, at least 99.4%, at least 99.5%, at least 99.6, but less than 100% sequence identity to the amino acid sequence of SEQ ID NO: 1 or SEQ ID NO: 2;
b) a polypeptide encoded by a polynucleotide that hybridizes under low, medium, or high stringency conditions with (i) sequence encoding the polypeptide of SEQ ID NO: 1 or SEQ ID NO: 2, or (ii) the full-length complement of (i);
c) a polypeptide encoded by a polynucleotide having at least 75% e.g., at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, at least 99.1%, at least 99.2%, at least 99.3%, at least 99.4%, at least 99.5%, at least 99.6, identity to sequence encoding the polypeptide of SEQ ID NO: 1 or SEQ ID NO: 2; and
d) a fragment of the polypeptide of SEQ ID NO: 1 or SEQ ID NO: 2, which has pectate lyase activity.

9. The variant according to any of the preceding paragraphs, wherein the variant comprises a substitution in one or more of positions selected from the group consisting of positions: 250, 176, 124, 325, 108 and 149.

10. The variant according to any of the preceding paragraphs, wherein the variant comprises a substitution to lysine or arginine in one or more of positions selected from the group consisting of positions: 48, 49, 108, 124 and 149.

11. The variant according to any of the preceding paragraphs, wherein the variant has improved stability in detergent (e.g., as shown in example 2 herein, e.g., using half-life improvement factor as a measure of stability in detergent or as shown in example 4 herein, e.g., using residual wash performance assay as a measure of stability in detergent) or improved thermal stability (e.g., as shown in example 5 herein, e.g., using thermal shift assay as a measure of thermal stability) compared to a parent enzyme.

12. The variant according to any of the preceding paragraphs, wherein the variant has a half-life improvement factor (HIF) of >1.0, e.g., HIF of >2.0, HIF of >3.0, HIF of >4.0, HIF of >5.0, HIF of >6.0, HIF of >7.0, HIF of >8.0, HIF of >9.0, HIF of >10.0, HIF of >11.0, HIF of >12.0, HIF of >13.0, HIF of >14.0, HIF of >15.0, HIF of >16.0, HIF of >17.0, HIF of >18.0.

13. The variant according to any of the preceding paragraphs, wherein the total number of alterations compared to SEQ ID NO 1 or SEQ ID NO: 2 is 1-20, e.g., 1-10 and 1-5, such as 1, 2, 3, 4, 5, 6, 7, 8, 9 or 10 alterations.

14. A composition comprising a variant of any of preceding paragraphs.

15. The composition of paragraph 14, wherein said composition is a cleaning or detergent composition, preferably a laundry or dish wash composition.

16. The composition according to any of preceding paragraphs further comprising one or more detergent components.

17. The composition of paragraph 16, wherein the detergent component is selected from the group consisting of: surfactants, hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants, and solubilizers.

18. The composition according to any of preceding paragraphs further comprising one or more additional enzymes.

19. The composition according to any of predecing paragraphs, further comprising one or more additional enzymes selected from the group consisting of: proteases, amylases, lichenases, lipases, cutinases, cellulases, endoglucanases, xyloglucanases, pectinases, pectin lyases, xanthanases, peroxidaes, haloperoxygenases, catalases, mannanases, oxidoreductases, hemicellulases, mannanases, xylanases, galactanases, arabinofuranosidases, esterases, arabinanases, another pectate lyase, DNases, perhydrolases, amylases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, or combinations thereof.

20. The composition according to any of preceding paragraphs, wherein said composition is a cleaning or detergent composition in form of a bar, a homogenous tablet, a tablet having two or more layers, a pouch having one or more compartments, a regular or compact powder, a granule, a paste, a gel, or a regular, compact or concentrated liquid.

21. Use of a pectate lyase variant or composition of any of preceding paragraphs, wherein said use is selected from the group comprising or consisting of:
i) use in cleaving a pectic substance, preferably said pectic substance comprises poly(1,4-alpha-D-galacturonide) or its derivative, ii) use in cleaning process, such as laundry or hard surface cleaning such as dish wash, iii) use in processing of textile and/or cellulosic fiber,
iv) use in enzymatic removal of cell-wall material from textile,
v) use in processing of wine or juice and
vi) use as an animal feed additive.
22. Use of a variant according to any of preceding paragraphs in a detergent composition, preferably said detergent composition is a laundry and/or dish wash detergent composition.
23. Use of a variant or composition according to any of preceding paragraphs for cleaving a pectic substance, preferably said pectic substance comprises poly(1,4-alpha-D-galacturonide) or its derivative.
24. Use of a variant or composition according to any of preceding paragraphs for processing of textile and/or cellulosic fiber.
25. Use of a variant or composition according to any of preceding paragraphs for enzymatic removal of cell-wall material from textile.
26. Use of a variant or composition according to any of preceding paragraphs for processing of wine or juice.
27. Use of a variant or composition according to any of preceding paragraphs as an animal feed additive.
28. Use of a variant or a composition according to any of preceding paragraphs in a cleaning process, such as laundry or hard surface cleaning such as dish wash.
29. Use of a variant or a composition according to any of preceding paragraphs, wherein said variant has an enzyme detergency benefit.
30. Use of a variant or a composition according to any of preceding paragraphs for washing or cleaning a textile and/or a hard surface such as dish wash including Automatic Dish Wash (ADW).
31. An enzymatic scouring method, comprising contacting cell-wall material with a pectate lyase variant or composition according to any of preceding paragraphs.
32. A method for enzymatic removal of cell-wall material from a textile, comprising contacting the textile with a pectate lyase variant or composition according to any of preceding paragraphs.
33. A method for removing a stain from a surface which comprises contacting the surface with a pectate lyase variant or composition according to any of preceding paragraphs.
34. A process of cleaving a pectic substance comprising applying the a pectate lyase variant or composition of any of preceding paragraphs to said pectic substance, preferably said pectic substance comprises poly(1,4-alpha-D-galacturonide) or its derivative.
35. The process of paragraph 34, wherein said pectic substance is on the surface of a textile or hard surface, such as dish wash.
36. A polynucleotide encoding the variant of any of the preceding paragraphs.
37. A nucleic acid construct or expression vector capable of expressing a polynucleotide of paragraph 36, preferably said nucleic acid construct or said expression vector comprising the polynucleotide of paragraph 36 operably linked to one or more control sequences that direct the production of the polypeptide in an expression host.
38. A microbial host cell transformed with the nucleic acid construct or the expression vector of paragraph 37.
39. A microbial host cell according to paragraph 38, wherein the cell is a bacterium, preferably a *Bacillus*, more preferably a *Bacillus subtilis*.
40. A recombinant host cell comprising the polynucleotide of paragraph 36, preferably said polynucleotide is operably linked to one or more control sequences that direct the production of the polypeptide, further preferably said recombinant host cell is an isolated recombinant host cell.
41. A method for producing (or obtaining) a pectate lyase variant according to any of preceding paragraphs, wherein a microbial host cell according to any of preceding paragraphs is cultured under conditions conductive to the expression and secretion of the variant, and recovering the variant.
42. A method for improving the detergent stability of a pectate lyase (e.g., a parent pectate lyase, e,g., having SEQ ID NO:1 or SEQ ID NO:2), comprising: introducing into said pectate lyase (e.g., said parent pectate lyase, e,g., having SEQ ID NO:1 or SEQ ID NO:2) an alteration(s) (e.g., a substitution(s), insertion(s) or deletion(s)) at one or more positions selected from the group consisting of positions (e.g., combinations of positions): 48, 49, 99, 108, 124, 149, 176, 229, 250, 257, 325, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+176+229+257+325+356, 229+250, 229+356, 49+99+124+176+229+250+257+325+356, 49+99+176+229+257+325+356, 49+99+176+229+250+257+325+356, 49+99+124+176+229+250+257+325+356, 49+99+108+124+176+229+250+257+325+356, 48+49+99+176+250+257+325+356, 49+99+176+250+325+257+356, 48+229, 229+257, 229+250, 229+356, 48+257, 250+257, 257+356, 48+250, 48+356, 250+356, 229+250+356, wherein each position corresponds to a position of the amino acid sequence of the pectate lyase having the amino acid sequence of SEQ ID NO:1, and wherein the pectate lyase (e.g., the altered pectate lyase, e.g., comprising said alteration(s) at one or more positions) has at least 75%, e.g., at least 80%, at least 85%, at least 90%, at least 95%, at least 96%, at least 97%, at least 98%, or at least 99%, at least 99.1%, at least 99.2%, at least 99.3%, at least 99.4%, at least 99.5%, at least 99.6, but less than 100% sequence identity to the amino acid sequence of SEQ ID NO:1 or SEQ ID NO:2.
43. The method according to paragraph 41, further comprising: introducing into a parent pectate lyase an alteration(s) (e.g., a substitution(s), insertion(s) or deletion(s)) at one or more positions selected from the group consisting of positions (e.g., combinations of positions): 48, 49, 99, 108, 124, 149, 176, 229, 250, 257, 325, 356, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 48+229, 229+257, 229+250, 229+356, 250+257, 257+356, 48+250, 48+356, 250+356, 48+49+99+176+257+325+356, 48+49+99+176+257+325+356, 49+99+124+176+257+325+356, 49+99+176+229+257+325+356, 229+250, 229+356, 49+99+124+176+229+250+257+325+356, 49+99+176+229+257+325+356, 49+99+176+229+250+257+325+356, 49+99+124+176+229+250+257+325+356, 49+99+108+124+176+229+250+257+325+356, 48+49+99+176+250+257+325+356, 49+99+176+250+325+257+356, 48+229, 229+257, 229+250, 229+356, 48+257, 250+257, 257+356, 48+250, 48+356, 250+356, 229+250+356, wherein the pectate lyase variant has an amino acid sequence which is at least 75%, e.g., at least 80%, at least 85%, at least 90%, at least 95%, at least 96%, at least 97%, at least 98%, or at least 99%, at least 99.1%, at least 99.2%, at least 99.3%, at least 99.4%, at least 99.5%, at least 99.6, but less than 100%, sequence identity to the amino acid sequence of SEQ ID NO:1 or SEQ ID NO:2.
44. The method of any of paragraphs 20-21, wherein said alteration is a substitution in one or more positions selected from the group consisting of positions: 48, 49, 108, 124 and 149, and wherein said substitution is with a positively charged amino acid, preferably said positively charged amino acid is lysine or arginine.
45. The method of any of paragraphs 42-43, wherein said alteration at one or more positions is selected from the group consisting of substitutions (e.g., combinations of substitutions): P48A, P48F, P48H, P48I, P48K, P48L, P48N, P48Q, P48R, P48S, P48T, P48W, P48Y, T49F, T49H, T49I, T49K, T49L, T49M, T49N, T49Q, T49R, T49V, T49W, T49Y, K99A, K99C, K99D, K99E, K99F, K99G, K99H, K99I, K99L, K99M, K99N, K99P, K99Q, K99S, K99T, K99V, K99W, K99Y, E108A, E108G, E108H, E108K, E108L, E108M, E108N, E108R, E108S, E108T, E108V, E108W, D124A, D124E, D124F, D124G, D124I, D124L, D124M, D124N, D124P, D124Q, D124R, D124S, D124T, D124V, D124W, S149K, S149L, S149R, S149W, S176A, S176C, S176D, S176E, S229I, S229K, S229L, S229M, S229Q, S229T, S229V, S229Y, I250A, I250G, I250L, I250M, I250N, I250S, I250T, K257A, K257C, K257D, K257H, K257I, K257L, K257M, K257Q, K257S, K257V, K257W, I325F, I325L, I325Y, Q356D, Q356E, Q356F, Q356G, Q356H, Q356I, Q356L, Q356N, Q356R, Q356T, Q356W, Q356Y, K99D+S176D+I325F, T49R+K99D+S176D+I325F+Q356F, T49R+K99D+S176D+K257L+I325F+Q356F, T49R+K99D+S176D+S229I+K257L+I325F+Q356F, K99D+S176D+I325F+Q356F, K99D+T49W+S176D+I325F+Q356F, K99D+D124W+S176D+I325F+Q356F, P48W+K99D+S176D+I325F+Q356F, K99D+E108N+S176D+I325F+Q356F, K99D+T49W+E108N+S176D+I325F+Q356F, P48W+S229I, S229I+K257L, S229I+I250N, S229I+Q356F, I250N+K257L, K257L+Q356F, P48W+I250N, P48W+Q356F, I250N+Q356F, P48W+T49W+K99D+S176D+K257L+I325F+Q356F, P48W+T49W+K99D+S176D+K257L+I325F+Q356F, T49R+K99D+D124W+S176D+K257L+I325F+Q356F, T49R+K99D+S176D+S229I+K257L+I325F+Q356F, S229I+I250N, S229I+Q356F, T49R+K99D+D124W+S176D+S229I+I250N+K257L+I325F+Q356F, T49R+K99D+S176D+S229I+K257L+I325F+Q356F, T49R+K99D+S176D+S229I+I250N+K257L+I325F+Q356F, T49R+K99D+D124W+S176D+S229I+I250N+K257L+I325F+Q356F, T49R+K99D+E108N+D124W+S176D+S229I+I250N+K257L+I325F+Q356F, P48W+T49R+K99D+S176D+I250N+K257L+I325F+Q356F, T49R+K99D+S176D+I250N+I325F+K257L+Q356F, P48W+S229I, S229I+K257L, S229I+I250N, S229I+Q356F, P48W+K257L, I250N+K257L, K257L+Q356F, P48W+I250N, P48W+Q356F and I250N+Q356F, S229I+I250N+Q356F.
46. A method for improving the detergent stability of a pectate lyase (e.g., a parent pectate lyase, e.g., having SEQ ID NO:1 or SEQ ID NO:2), comprising: introducing into said pectate lyase (e.g., said parent pectate lyase, e.g., having SEQ ID NO:1 or SEQ ID NO:2) an alteration(s) (e.g., a substitution(s), insertion(s) or deletion(s)) at one or more positions selected from the group consisting of positions (e.g., combinations of positions): 250, 176, 124, 108, 149, and 325, wherein each position corresponds to a position of the amino acid sequence of the pectate lyase having the amino acid sequence of SEQ ID NO:1, and wherein the pectate lyase (e.g., the altered pectate lyase, e.g., comprising said alteration(s) at one or more positions) has at least 75%, e.g., at least 80%, at least 85%, at least 90%, at least 95%, at least 96%, at least 97%, at least 98%, or at least 99%, at least 99.1%, at least 99.2%, at least 99.3%, at least 99.4%, at least 99.5%, at least 99.6, but less than 100% sequence identity to the amino acid sequence of SEQ ID NO:1 or SEQ ID NO:2.
47. The method of any of preceding paragraphs, wherein the parent pectate lyase is selected from the group consists of:
a) a polypeptide having at least 75%, e.g., at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6, or 100% sequence identity to the amino acid sequence of SEQ ID NO: 1 or SEQ ID NO: 2;
b) a polypeptide encoded by a polynucleotide that hybridizes under medium, or high stringency conditions with (i) sequence encoding the polypeptide of SEQ ID NO: 1 or SEQ ID NO: 2, or (ii) the full-length complement of (i);
c) a polypeptide encoded by a polynucleotide having at least 75% identity to sequence encoding the polypeptide of SEQ ID NO: 1 or SEQ ID NO: 2;
d) a fragment of the polypeptide of SEQ ID NO: 1 or SEQ ID NO: 2, which has pectate lyase activity.
48. The method of any of preceding paragraphs, wherein said alteration at one or more positions provides a variant having a half-life improvement factor (HIF) of >1.0, e.g., HIF of >2.0, HIF of >3.0, HIF of >4.0, HIF of >5.0, HIF of >6.0, HIF of >7.0, HIF of >8.0, HIF of >9.0, HIF of >10.0, HIF of >11.0, HIF of >12.0, HIF of >13.0, HIF of >14.0, HIF of >15.0, HIF of >16.0, HIF of >17.0, HIF of >18.0.

Methods

Microtiter Assay for Quantification of Pectate Lyase Activity

Pectate lyase cleaves polygalacturonic acid through a trans elimination mechanism. This means that it leaves a double C—C bond for each substrate split. This bond absorbs at 235 nm allowing direct detection of pectate lyase action on soluble polygalacturonic acid by measuring absorbance at that wavelength.

An enzyme sample is diluted in assay buffer (100 mM Tris-HCl, 0.68 mM $CaCl_2$), pH 8.0) to a concentration between 5 and 100 ng/ml. If the enzyme sample contains detergent it should be diluted at least a 1000-fold with respect to detergent. 100 µl of the enzyme buffer dilution is mixed with 100 µl substrate (1% (w/v) polygalacturonic acid, e.g., P-3850 from Sigma, stirred in assay buffer for at least 15 min and centrifuged for 5 min at 2300 g, supernatant is used) in a heating plate and heated to 40° C. for 10 min in a heating block, preferably a PCR machine or equipment of equivalent accuracy and heating speeds.

100 µl enzyme/substrate solution is mixed with 100 µl stop reagent (50 mM $H_3PO_4$) in a UV-transparent microtiter plate. The UV plate is shaken briefly and gently, and the absorbance at 235 nm is measured in a microtiter spectrometer (e.g., Molecular Devices, SpectraMAX 190). The absorbance readings are corrected for background absorbance by subtracting the absorbance of a control sample, run without enzyme added, to all measured values.

A standard curve based on the activity of the pectate lyase of SEQ ID NO:2 in WO 2003/095638 (from *Bacillus subtilis* deposited as IFO 3134) was linear between 2.5 and 100 ng/ml enzyme in the reaction mixture:

| Enzyme dose (ng/ml) | Absorbance at 235 nm (AU), background subtracted |
|---|---|
| 0 | 0.00 |
| 2.5 | 0.03 |
| 5 | 0.07 |
| 10 | 0.16 |
| 15 | 0.26 |
| 25 | 0.42 |
| 50 | 0.85 |
| 100 | 1.83 |

Alternatively, catalytic activity of pectate lyase can be determined by the viscosity assay, APSU.

Viscosity Assay, APSU

APSU units: The APSU assay measures the change in viscosity of a solution of polygalacturonic acid in the absence of added calcium ions. A 5% w/v solution of sodium polygalacturonate (e.g., Sigma P-1879) is solubilised in 0.1 M glycine buffer, pH 10.4 ml of this solution are preincubated for 5 min at 40° C. Then, 250 microlitre of the enzyme (or enzyme dilution) are added, after which the reaction is mixed for 10 sec on a mixer at the highest speed and incubated for 20 min at 40° C. or at another temperature.

Viscosity is measured using a viscometer (e.g., the MIVI 600 viscometer, Sofraser, 45700 Villemandeur, France). Viscosity is measured as mV after 10 sec. For calculation of APSU units the following standard curve is used:

| APSU/ml | 0.00 | 4.00 | 9.00 | 14.00 | 19.00 | 24.00 | 34.00 | 49.00 | 99.00 |
|---|---|---|---|---|---|---|---|---|---|
| mV | 300 | 276 | 249 | 227 | 206 | 188 | 177 | 163 | 168 |

Test Materials

Wash performance of pectate lyases was investigated on test materials (swatches) obtained from Center for Testmaterials BV, P.O. Box 120, 3133 KT Vlaardingen, the Netherlands. A commercial "EU heavy duty liquid detergent" was purchased in a British supermarket in February 2013.

| Composition of laundry powder model detergent A: |
|---|
| Sodium citrate dihydrate 32.3% |
| Sodium-LAS 24.2% |
| Sodium lauryl sulfate 32.2% |
| Neodol 25-7 (alcohol ethoxylate) 6.4% |
| Sodium sulfate 4.9% |

The present invention is further described by the following examples that should not be construed as limiting the scope of the invention.

EXAMPLES

Example 1

Cloning, Fermentation, and Purification of Pectate Lyase Variants

Based on the pectate lyase backbone with the amino acid sequence shown in SEQ ID NO:1 the variants as disclosed below were prepared by expression in *B. subtilis*. All DNA manipulations and transformations were performed using standard methods of molecular biology.

The recombinant *B. subtilis* constructs encoding pectate lyase variants were used to inoculate shakeflasks containing a rich media (100 g/L sucrose, 40 g/L crust soy (soy bean flour), 10 g/L $Na_2HPO_4.12H_2O$, 0.1 ml/L Dowfax63N10 (e.g., Dow for short). Dowfax63N1 is a nonionic surfactant. Cultivation for 4 days at 30° C. shaking with 220 rpm. The fermentation cultures of *B. subtilis* expressing pectate lyase variants were centrifuged at 13000 rpm for 20 min and the supernatants were hereafter filtered through a 0.22 µm filter. The filtrates were added ammonium sulfate (AmS) to a concentration of 1 M and applied to a MEP column pre-equilibrated in 50 mM HEPES, 1 M AmS, pH 7. Unbound material was washed off the column and bound protein was subsequently eluted using 100 mM $CH_3COOH$, pH 4.5. The eluate was hereafter buffer exchanged using a Sephadex G-25 column into 25 mM $CH_3COOH$, pH 4.5 and applied to a Source 15S column pre-equilibrated in the same buffer. After washing off unbound protein, the pectate lyase was eluted using a linear gradient from 0 to 1 M NaCl in 25 mM $CH_3COOH$, pH 4.5.

The following variants of the pectate lyase backbone with the amino acid sequence shown in SEQ ID NO:1 were prepared: P48A, P48F, P48H, P48I, P48K, P48L, P48N, P48Q, P48R, P48S, P48T, P48W, P48Y, T49F, T49H, T49I, T49K, T49L, T49M, T49N, T49Q, T49R, T49V, T49W, T49Y, K99A, K99C, K99D, K99E, K99F, K99G, K99H, K99I, K99L, K99M, K99N, K99P, K99Q, K99S, K99T, K99V, K99W, K99Y, E108A, E108G, E108H, E108K, E108L, E108M, E108N, E108R, E108S, E108T, E108V, E108W, D124A, D124E, D124F, D124G, D124I, D124L, D124M, D124N, D124P, D124Q, D124R, D124S, D124T, D124V, D124W, S149K, S149L, S149R, S149W, S176A, S176C, S176D, S176E, S229I, S229K, S229L, S229M, S229Q, S229T, S229V, S229Y, I250A, I250G, I250L, I250M, I250N, I250S, I250T, K257A, K257C, K257D, K257H, K257I, K257L, K257M, K257Q, K257S, K257V, K257W, I325F, I325L, I325Y, Q356D, Q356E, Q356F, Q356G, Q356H, Q356I, Q356L, Q356N, Q356R, Q356T, Q356W, Q356Y, K99D+S176D+I325F, T49R+K99D+S176D+I325F+Q356F, T49R+K99D+S176D+K257L+I325F+Q356F, T49R+K99D+S176D+S229I+K257L+I325F+Q356F, K99D+S176D+I325F+Q356F, K99D+T49W+S176D+I325F+Q356F, K99D+D124W+S176D+I325F+Q356F, P48W+K99D+S176D+I325F+Q356F, K99D+E108N+S176D+I325F+Q356F, K99D+T49W+E108N+S176D+I325F+Q356F, P48W+S229I, S229I+K257L, S229I+I250N, S229I+Q356F, I250N+K257L, K257L+Q356F, P48W+I250N, P48W+Q356F, I250N+Q356F, P48W+T49R+K99D+S176D+K257L+I325F+Q356F, P48W+T49W+K99D+S176D+K257L+I325F+Q356F, T49R+K99D+D124W+S176D+K257L+I325F+Q356F, T49R+K99D+S176D+S229I+K257L+I325F+Q356F, S229I+I250N, S229I+Q356F, T49R+K99D+D124W+S176D+S229I+I250N+K257L+I325F+Q356F, T49R+K99D+S176D+S229I+K257L+I325F+Q356F, T49R+K99D+S176D+S229I+I250N+K257L+I325F+Q356F, T49R+K99D+D124W+S176D+S229I+I250N+K257L+I325F+Q356F, T49R+K99D+E108N+D124W+S176D+S229I+I250N+K257L+I325F+Q356F, P48W+T49R+K99D+S176D+I250N+K257L+I325F+Q356F, T49R+K99D+S176D+I250N+I325F+K257L+Q356F, P48W+S229I, S229I+K257L, S229I+I250N, S229I+Q356F, P48W+K257L, I250N+K257L, K257L+Q356F, P48W+I250N, P48W+Q356F and S229I+I250N+Q356F (e.g., as described herein in Table 1 of Example 2, Table 2 of Example 3, Table 3 of Example 3, Table 4 of Example 4, Table 5 of Example 5 below).

Example 2

Measuring the Stability of Pectate Lyase Variants in Liquid Detergent

The in-detergent stability of pectate lyase variants was assessed by measuring the activity of the variants after incubation of an enzyme-detergent mixture. Half-life improvement factors (HIFs) were determined in 15% Model A detergent.

Residual activity assay: 20 microliter of an enzyme solution (culture supernatant) was mixed with 30 microliter of a "Model A detergent" (prediluted to 25% v/v in water) in a 384 well microplate (polystyrene). From each well 10 microliter was transferred to two new 384 well microplates. One of the two identical plates was stored at 5° C. while the other was incubated at 45.5° C. for 16 hours. After incubation, 40 microliter of assay buffer (100 mM Tris-HCL, 0.68 mM $CaCl_2$), pH 8.0) was added to the samples in both plates and mixed vigorously. All samples in both plates were diluted further a factor 8 with assay buffer.

The plate stored at 5° C. was diluted further a factor 5 in a weak detergent solution (0.47% v/v detergent in assay buffer). The enzymatic activity was measured by mixing 20 micro liter of the diluted enzyme-detergent mixture with 20 micro liter freshly prepared substrate solution (1% polygalacturonic acid in assay buffer) in a UV-transparent 384 well microplate and measuring the absorbance at 235 nm using a spectrophotometer.

The residual activity was calculated as the enzymatic activity of the sample incubated at 45.5° C. for 16 hours relative to the enzymatic activity in the sample stored at 5° C. Residual activity (RA)=100%*Activity [sample at 45.5° C.]/Activity [sample at 5° C.].

Calculating Half-Life Improvement Factors (HIFs):

Residual activity for variants (RA-var) is compared to residual activity for the Backbone (SEQ ID NO:1) reference (RA-Bb). A Half-life value (T½(in hours)) can be calculated for the Backbone/reference and samples, because the degradation follows an exponential decay and the incubation-time (hours) is known. A half-life improvement factor (HIF) is calculated as T½(Variant)/T½(Bb). Since both samples are incubated for the same period of time, the equation can be simplified and reduced to: HIF=Ln(RA-Bb/100)/Ln(RA-var/100). The obtained HIF values are listed in Table 1 below.

TABLE 1

Half-life improvement factors (HIFs) determined after incubation of culture supernatants in 15% model A detergent at 45° C.

| Substitution | P48 | T49 | K99 | E108 | D124 | S149 | S176 | S229 | I250 | K257 | I325 | Q356 |
|---|---|---|---|---|---|---|---|---|---|---|---|---|
| A | 1.5 | | 2.1 | 2 | 2.3 | | 1.2 | | 2.2 | 2.1 | | |
| C | | | 3.2 | | | | 2.8 | | | 4.7 | | |
| D | | | 2.5 | | | | 2.5 | | | 4.2 | | 2 |
| E | | | 2.5 | | 1.4 | | 2.5 | | | | | 2.5 |
| F | 1.5 | 1.7 | 2.3 | | 2.8 | | | | | | 4.2 | 2.7 |
| G | | | 2.1 | 1.7 | 2.7 | | | | 2.3 | | | 1.7 |
| H | 1.2 | 1.5 | 2.2 | 1.8 | | | | | | 4.8 | | 1.6 |
| I | 1.3 | 1.3 | 2 | | 2.5 | | | 5.9 | | 2 | | 1.6 |
| K | 3.5 | 3.9 | | 3.6 | | 3.6 | 2.1 | | | | | |
| L | 1.4 | 1.7 | 2 | 1.8 | 2.6 | 2.1 | 1.7 | 3.1 | 4 | | 1.4 | 1.9 |
| M | | 1.2 | 2 | 1.7 | 2.7 | | | 1.5 | 2.3 | 6.1 | | |
| N | 1.4 | 1.2 | 2.3 | 2.1 | 2.5 | | | | 3.2 | | | 1.6 |
| P | | 2.2 | | 2.2 | | | | | | | | |
| Q | 1.5 | 1.6 | 2.3 | | 2.1 | | | 1.9 | | 5.3 | | |
| R | 5.2 | 4.3 | | 5.7 | 4.9 | 3.4 | | | | | | 1.9 |
| S | 1.4 | | 2.2 | 1.9 | 2.7 | | | | 2.2 | 2.1 | | |
| T | 1.5 | | 1.9 | 1.9 | 2.4 | | | 1.5 | 2.8 | | | 1.6 |
| V | | 1.2 | 2.2 | 1.8 | 2.3 | | | 3.7 | | 1.7 | | |
| W | 2.6 | 3.7 | 1.7 | 2 | 3.3 | 1.2 | | | | 1.5 | | 1.8 |
| Y | 2 | 2 | 1.8 | | 2.3 | | | 4.3 | | | 1.6 | 2.3 |

Especially pronounced was a substitution to an amino acid carrying positive charges, i.e., to lysine or arginine, in positions 48, 49, 108, 124 and 149 with respect to improved stability in detergents and/or improved thermal stability.

Example 3

Determination of Stability Improvement of the Variants in 90% Liquid Detergent Half-life improvements factors (HIFs) were determined in 90% "EU heavy duty liquid detergent". The detergent stability of the pectate lyase variants was assessed by measuring the activity of the variants after incubation of an enzyme-detergent mixture as described below. Half-life improvement factors (HIFs) determination assay: Samples were either purified enzyme diluted to 1000 ppm or shake-flask culture supernatant. 20 microliter sample was mixed with 180 microliter "EU heavy duty liquid detergent".

Aliquots of the mixtures were incubated at 55° C. (purified samples) or 56° C. (supernatants) in a PCR-machine (PTC200). As a function of time, aliquots were diluted a factor 250 with assay buffer and analyzed for content on enzymatic activity—as described in Example 2 above. Thus for each variant, information about degradation as a function of time is obtained. Exponential decay of enzymatic activity is expected and was observed for all samples.

The Excel (Microsoft version 2010) "Logest" function was used to calculate the exponential curve that best fits a supplied set of y- and x-values (y=b*mAx, wherein operator "A" (or caret) raises a number to a power, and operator "*" (or asterisk) multiplies numbers). Incubation time was used as X-values and enzymatic activity was Y-values, to get best fit of data to exponential decay: y=b*mAx and for calculate the exponential decay constant (k=Ln(m)) and finally the T½ time (T½=Ln2/k). The half-life improvement factor is finally calculated as: HIF=T½(variant)/T½(backbone). The obtained HIF values are listed in Tables 2 (purified samples) and 3 (supernatant samples) below.

TABLE 2

Half-life improvement factor (HIF) determined after incubation of purified enzymes in 90% EU heavy duty liquid detergent at 55° C.

| Substitutions | HIF |
|---|---|
| Backbone (SEQ ID NO: 1) | 1.0 |
| S229I | 9.6 |
| S176D | 1.1 |
| I325F | 1.8 |
| I250L | 6.1 |
| T49R | 3.8 |
| I250N | 8.2 |
| I250T | 4.3 |
| K99D + S176D + I325F | 1.6 |
| T49R + K99D + S176D + I325F + Q356F | 2.2 |
| T49R + K99D + S176D + K257L + I325F + Q356F | 1.7 |
| T49R + K99D + S176D + S229I + K257L + I325F + Q356F | 18.0 |
| K99D + S176D + I325F + Q356F | 2.0 |
| K99D + T49W + S176D + I325F + Q356F | 1.1 |
| K99D + D124W + S176D + I325F + Q356F | 1.2 |
| P48W + K99D + S176D + I325F + Q356F | 2.6 |
| K99D + E108N + S176D + I325F + Q356F | 2.2 |
| K99D + T49W + E108N + S176D + I325F + Q356F | 1.1 |

TABLE 3

Half-life improvement factor (HIF) determined after incubation of culture supernatants in 90% EU heavy duty liquid detergent at 56° C.

| Substitutions | HIF |
|---|---|
| Backbone (SEQ ID NO: 1) | 1.0 |
| S229I | 12.0 |
| P48W + S229I | 9.1 |
| S229I + K257L | 8.8 |
| S229I + I250N | 18.5 |
| S229I + Q356F | 14.5 |
| I250N + K257L | 8.6 |
| K257L + Q356F | 1.4 |
| P48W + I250N | 7.9 |
| P48W + Q356F | 1.6 |
| I250N + Q356F | 18.5 |

Variants with the following combination of substitutions P48W+T49R+K99D+S176D+K257L+I325F+Q356F, P48W+T49W+K99D+S176D+K257L+I325F+Q356F and T49R+K99D+D124W+S176D+K257L+I325F+Q356F were also fermented, purified and found to have improved residual activity after storage in liquid detergent.

Example 4

Determination of Stability in Liquid Detergent

The storage stability of pectate lyase variants was measured by residual wash performance after storage in model A liquid detergent (Table 4). The stability was determined by storage of pectate lyase variants for 4 weeks at 37° C. in the liquid detergent followed by wash performance evaluation in a mini-Terg-O-tometer (mini-TOM) wash assay using the stains C—S-53 (pectate with pigment on cotton) and PC—S-53 (pectate with carbon black on polyester/cotton) purchased from CFT. Mini-TOM wash is similar to TOM wash, however, 400 mL beakers are used instead of regular 2000 mL beakers. The remaining conditions are unchanged. The mini-TOM wash was conducted for 30 min at 30° C. with 120 RPM using 15° dH water (Ca:Mg:HCO$_3^-$=4:1:7.5) and a detergent dosage of 3.33 g/L in a total wash volume of 200 mL. After wash stains were rinsed, dried and intensities were quantified using a Digi-Eye spectrophotometer.

Specifically, each pectate lyase was dosed at 0.015 mg enzyme protein/g detergent in model A liquid detergent (corresponding to 0.05 ppm enzyme in wash) in closed glass containers and incubated in a heating cabinet at 37° C. for 4 weeks. Identical reference samples were placed at −18° C. instead. After 4 weeks the wash performance of the variants stored at 37° C. was compared to the wash performance of the samples stored at −18° C. to calculate residual wash performance for each variant. The residual wash performance of each variant was calculated as: Residual wash performance=($\Delta INT_{37° C.}$)/($\Delta INT_{−18° C.}$), where $\Delta$LINT was calculated as the intensity obtained between the specific condition and a corresponding no enzyme blank.

TABLE 4

Residual wash performance (WP) of purified pectate lyase variants after storage in liquid model A detergent for 4 weeks at 37° C. measured by mini-TOM wash.

| Substitutions | Residual WP |
|---|---|
| Backbone (SEQ ID NO: 1) | 28% |
| S229I | 79% |
| E108N | 49% |
| I250N | 74% |
| K257L | 33% |
| T49R + K99D + S176D + S229I + K257L + I325F + Q356F | 55% |

Variants with the following combination of substitutions S229I+I250N, S229I+Q356F and T49R+K99D+D124W+S176D+S229I+I250N+K257L+I325F+Q356F were also fermented, purified and found to have improved residual wash performance as measured by mini-TOM wash after storage in liquid detergent.

Example 5

Determination of Thermal Stability

Thermal stability was determined using protein thermal unfolding analysis (TSA, Thermal shift assay) (Table 5).

Protein thermal unfolding was monitored with Sypro Orange (In-vitrogen, S-6650) using a real-time PCR instrument (e.g., Applied Biosystems; Step-One-Plus). In a 96-well white PCR-plate, 15 microliter sample (purified enzyme 100 ppm) in 100 mM HEPES; 20 mM EDTA pH 8.0 was mixed (1:1) with Sypro Orange (Conc.=10×; stock solution from supplier=5000×). The plate was sealed with an optical PCR seal. The PCR instrument was set at a scan-rate of 76° C. per hr, starting at 25° C. and finishing at 96° C. Fluorescence was monitored every 20 seconds using in-built LED blue light for excitation and ROX-filter (610 nm, emission). Tm-values were calculated as the maximum value of the first derivative (dF/dK) (Gregory et al; *J Biomol Screen* 2009 14: 700).

TABLE 5

Protein thermal unfolding analysis in HEPES buffer using TSA. Tm (° C.)

| Substitutions | Tm |
|---|---|
| Backbone (SEQ ID NO: 1) | 71.1 |
| S229I | 75.0 |
| S176D | 73.0 |
| I325F | 72.6 |
| Q356F | 71.4 |
| I250L | 74.2 |
| T49R | 71.4 |
| S229V | 77.1 |
| S229K | 74.2 |
| I250N | 76.3 |
| K257L | 74.0 |
| K257D | 73.0 |
| P48W | 73.0 |
| D124W | 71.2 |
| I250T | 77.3 |
| K99D | 72.2 |
| K99V | 72.2 |
| Q356E | 73.0 |
| S149R | 71.4 |
| T49R + K99D + S176D + S229I + K257L + I325F + Q356F | 76.6 |
| T49R + K99D + S176D + S229I + I250N + K257L + I325F + Q356F | 78.4 |
| I250N + K257L + I325F + Q356F | 77.5 |
| T49R + K99D + D124W + S176D + S229I + I250N + K257L + I325F + Q356F | 74.7 |
| T49R + K99D + E108N + D124W + S176D + S229I + I250N + K257L + I325F + Q356F | 74.9 |
| P48W + T49R + K99D + S176D + I250N + K257L + I325F + Q356F | 76.5 |
| T49R + K99D + S176D + I250N + I325F + K257L + Q356F | 76.7 |
| P48W + S229I | 77.9 |
| S229I + K257L | 78.8 |
| S229I + I250N | 77.1 |
| S229I + Q356F | 73.4 |
| P48W + K257L | 77.1 |
| I250N + K257L | 73.8 |
| K257L + Q356F | 75.9 |
| P48W + I250N | 73.0 |
| P48W + Q356F | 76.3 |
| I250N + Q356F | |

---

The invention claimed is:

1. A pectate lyase variant, wherein said variant has pectate lyase activity and comprises an alteration at one or more positions selected from the group consisting of: 250, 176, 124, 325, 108, 149, 99+176+325, 49+99+176+325+356, 49+99+176+257+325+356, 49+99+176+229+257+325+356, 99+176+325+356, 99+49+176+325+356, 99+124+176+325+356, 48+99+176+325+356, 99+108+176+325+356, 99+49+108+176+325+356, 229+250, 250+257, 48+250, 250+356, 48+49+99+176+257+325+356, 48+49+99+176+257+325+356, 49+99+124+176+257+325+356, 49+99+124+176+229+250+257+325+356, 49+99+176+229+250+257+325+356, 49+99+108+124+176+229+250+257+325+356, 48+49+99+176+250+257+325+356, 49+99+176+250+325+257+356, and 229+250+356, wherein each position corresponds to a position of the amino acid sequence of the pectate lyase having the amino acid sequence of SEQ ID NO:1, and wherein the variant has at least 90%, but less than 100% identity to the amino acid sequence of SEQ ID NO:1.

2. The variant of claim 1, which is a variant of a parent pectate lyase having at least 95% sequence identity to the amino acid sequence of SEQ ID NO:1.

3. The variant according to claim 1, wherein said alteration is a substitution with a positively charged amino acid.

4. The variant according to claim 1, wherein the variant comprises one or more substitutions selected from the group consisting of: E108A, E108G, E108H, E108K, E108L, E108M, E108N, E108R, E108S, E108T, E108V, E108W, D124A, D124E, D124F, D124G, D124I, D124L, D124M, D124N, D124P, D124Q, D124R, D124S, D124T, D124V, D124W, S149K, S149L, S149R, S149W, S176A, S176C, S176D, S176E, I250A, I250G, I250L, I250M, I250N, I250S, I250T, I325F, I325L, I325Y, K99D+S176D+I325F, T49R+K99D+S176D+I325F+Q356F, T49R+K99D+S176D+K257L+I325F+Q356F, 49R+K99D+S176D+S229I+K257L+I325F+Q356F, K99D+S176D+I325F+Q356F, K99D+T49W+S176D+I325F+Q356F, K99D+D124W+S176D+I325F+Q356F, P48W+K99D+S176D+I325F+Q356F, K99D+E108N+S176D+I325F+Q356F, K99D+T49W+E108N+S176D+I325F+Q356F, S229I+I250N, I250N+K257L, P48W+I250N, I250N+Q356F, P48W+T49R+K99D+S176D+K257L+I325F+Q356F, P48W+T49W+K99D+S176D+K257L+I325F+Q356F, T49R+K99D+D124W+S176D+K257L+I325F+Q356F, T49R+K99D+S176D+S229I+K257L+I325F+Q356F, S229I+I250N, T49R+K99D+D124W+S176D+S229I+I250N+K257L+I325F+Q356F, T49R+K99D+S176D+S229I+K257L+I325F+Q356F, T49R+K99D+S176D+S229I+I250N+K257L+I325F+Q356F, T49R+K99D+D124W+S176D+S229I+I250N+K257L+I325F+Q356F, T49R+K99D+E108N+D124W+S176D+S229I+I250N+K257L+I325F+Q356F, P48W+T49R+K99D+S176D+

I250N+K257L+I325F+Q356F, T49R+K99D+S176D+ I250N+I325F+K257L+Q356F, and S229I+I250N+Q356F.

5. A pectate lyase variant comprising an alteration at one or more positions selected from the group consisting of positions 250, 176, 124, 108, 149, and 325, wherein numbering is according to SEQ ID NO: 1, and wherein the alteration(s)
is a substitution of the amino acid which occupies the position with a different amino acid,
and wherein each position corresponds to a position of the amino acid sequence of the pectate lyase having the amino acid sequence of SEQ ID NO: 1, and wherein the variant pectate lyase has at least 90% identity to the amino acid sequence of SEQ ID NO: 1.

6. The variant of claim 5, which is a variant of a parent pectate lyase having at least 95% sequence identity to the amino acid sequence of SEQ ID NO:1.

7. The variant according to claim 1, wherein the variant has improved stability in detergent or improved thermal stability compared to a parent enzyme.

8. A composition comprising the variant of claim 1.

9. The composition of claim 8, wherein said composition is a cleaning or detergent composition.

10. The composition according to claim 8, further comprising:
i) one or more detergent components selected from the group consisting of: surfactants, hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants, and solubilizers; and/or
ii) one or more additional enzymes selected from the group consisting of: proteases, amylases, lichenases, lipases, cutinases, cellulases, endoglucanases, xyloglucanases, pectinases, pectin lyases, xanthanases, peroxidases, haloperoxygenases, catalases, mannanases, oxidoreductases, hemicellulases, xylanases, galactanases, arabinofuranosidases, esterases, arabinanases, pectate lyases, DNases, perhydrolases, betaglucanases, xanthan lyases, acyl transferases, phospholipases, laccases, aryl esterases, alpha-amylases, glucoamylases, keratinases, reductases, oxidases, phenoloxidases, lipoxygenases, ligninases, carrageenases, pullulanases, tannases, arabinosidases, hyaluronidases, chondroitinases, pectin acetyl esterases, polygalacturonases, rhamnogalacturonases, endo-beta-mannanases, exo-beta-mannanases, pectin methylesterases, cellobiohydrolases, transglutaminases, or combinations thereof.

11. A polynucleotide encoding the variant of claim 1.

12. An isolated host cell comprising the polynucleotide of claim 11.

13. A method for improving the detergent stability of a parent pectate lyase, comprising: introducing into said parent pectate lyase an alteration at one or more positions selected from the group consisting of:108, 124, 149, 176, 250, 325, 99+176+325, 49+99+176+325+356, 49+99+176+ 257+325+356, 49+99+176+229+257+325+356, 99+176+ 325+356, 99+49+176+325+356, 99+124+176+325+356, 48+99+176+325+356, 99+108+176+325+356, 99+49+108+ 176+325+356, 229+250, 50+257, 48+250, 250+356, 48+49+99+176+257+325+356, 48+49+99+176+257+325+ 356, 49+99+124+176+257+325+356, 49+99+176+229+ 257+325+356, 229+250, 229+356, 49+99+124+176+229+ 250+257+325+356, 49+99+176+229+257+325+356, 49+99+176+229+250+257+325+356, 49+99+124+176+ 229+250+257+325+356, 49+99+108+124+176+229+250+ 257+325+356, 48+49+99+176+250+257+325+356, 49+99+ 176+250+325+257+356, and 229+250+356, wherein each position corresponds to a position of the amino acid sequence of the pectate lyase having the amino acid sequence of SEQ ID NO:1, and wherein the altered pectate lyase has at least 90%, but less than 100% sequence identity to the amino acid sequence of SEQ ID NO:1, and incorporating the pectate lyase into a detergent composition.

14. The method of claim 13, wherein said alteration at one or more positions is selected from the group consisting of: E108A, E108G, E108H, E108K, E108L, E108M, E108N, E108R, E108S, E108T, E108V, E108W, D124A, D124E, D124F, D124G, D124I, D124L, D124M, D124N, D124P, D124Q, D124R, D124S, D124T, D124V, D124W, S149K, S149L, S149R, S149W, S176A, S176C, S176D, S176E, I250A, I250G, I250L, I250M, I250N, I250S, I250T, I325F, I325L, I325Y, K99D+S176D+I325F, T49R+K99D+S176D+ I325F+Q356F, T49R+K99D+S176D+K257L+I325F+ Q356F, T49R+K99D+S176D+S229I+K257L+I325F+ Q356F, K99D+S176D+I325F+Q356F, K99D+T49W+ S176D+I325F+Q356F, K99D+D124W+S176D+I325F+ Q356F, P48W+K99D+S176D+I325F+Q356F, K99D+ E108N+S176D+I325F+Q356F, K99D+T49W+E108N+ S176D+I325F+Q356F, S229I+I250N, I250N+K257L, P48W+I250N, I250N+Q356F, P48W+T49R+K99D+ S176D+K257L+I325F+Q356F, P48W+T49W+K99D+ S176D+K257L+I325F+Q356F, T49R+K99D+D124W+ S176D+K257L+I325F+Q356F, T49R+K99D+S176D+ S229I+K257L+I325F+Q356F, S229I+I 250N, T49R+ K99D+D124W+S176D+S229I+I250N+K257L+I325F+ Q356F, T49R+K99D+S176D+S229I+K257L+I325F+ Q356F, T49R+K99D+S176D+S229I+I250N+K257L+ I325F+Q356F, T49R+K99D+D124W+S176D+S229+ I250N+K257L+I325F+Q356F, T49R+K99D+E108N+ D124W+S176D+S229I+I250N+K257L+I325F+Q356F, P48W+T49R+K99D+S176D+I250N+K257L+I325F+ Q356F, T49R+K99D+S176D+I250N+I325F+K257L+ Q356F, and S229I+I250N+Q356F.

15. A method for improving the detergent stability of a pectate lyase, comprising: introducing into said pectate lyase a substitution at one or more positions selected from the group consisting of positions: 250, 176, 124, 108, 149, and 325, wherein each position corresponds to a position of the amino acid sequence of the pectate lyase having the amino acid sequence of SEQ ID NO: 1, and wherein the pectate lyase has at least 90% sequence identity to the amino acid sequence of SEQ ID NO:1 or SEQ ID NO:2, and incorporating the pectate lvase into a detergent composition.

16. The method of claim 13, wherein the parent pectate lyase is a polypeptide having at least 95% sequence identity to the amino acid sequence of SEQ ID NO: 1.

17. The method of claim 1, wherein said alteration at one or more positions provides a variant having a half-life improvement factor (HIF) of >1.0 compared to the parent pectate lyase.

* * * * *

SEQUENCE LISTING

<160> NUMBER OF SEQ ID NOS: 2

<210> SEQ ID NO 1
<211> LENGTH: 399
<212> TYPE: PRT
<213> ORGANISM: Artificial Sequence
<220> FEATURE:
<223> OTHER INFORMATION: The parent pectate lyase which is a variant of
      the pectate lyase from Bacillus subtilis disclosed in WO
      2002/09274.

<400> SEQUENCE: 1

```
Ala Asp Leu Gly His Gln Thr Leu Glu Ser Asn Asp Gly Trp Gly Ala
1               5                   10                  15

Tyr Ser Thr Gly Thr Thr Gly Gly Ser Lys Ala Ser Ser His Val
            20                  25                  30

Tyr Thr Val Ser Asn Arg Asn Gln Leu Val Ser Ala Leu Gly Lys Pro
        35                  40                  45

Thr Asn Thr Thr Pro Lys Ile Ile Tyr Ile Lys Gly Thr Ile Asp Phe
    50                  55                  60

Asn Val Asp Asp Asn Leu Lys Pro Leu Gly Leu Asn Asp Tyr Lys Asp
65                  70                  75                  80

Pro Glu Tyr Asp Leu Asp Lys Tyr Leu Lys Ala Tyr Asp Pro Ser Thr
                85                  90                  95

Trp Gly Lys Lys Glu Pro Ser Gly Pro Leu Glu Glu Ala Arg Ala Arg
            100                 105                 110

Ser Gln Lys Asn Gln Lys Ala Arg Val Met Val Asp Ile Pro Ala Asn
        115                 120                 125

Thr Thr Ile Val Gly Ser Gly Thr Asn Ala Ile Ile Val Gly Gly Asn
    130                 135                 140

Phe His Ile Lys Ser Asp Asn Val Ile Ile Arg Asn Ile Glu Phe Gln
145                 150                 155                 160

Asp Ala Tyr Asp Tyr Phe Pro Gln Trp Asp Pro Thr Asp Gly Ser Ser
                165                 170                 175
```

```
Gly Asn Trp Asn Ser Gln Tyr Asp Asn Ile Thr Ile Asn Gly Gly Thr
            180                 185                 190

His Ile Trp Ile Asp His Cys Thr Phe Asn Asp Gly Ser Arg Pro Asp
            195                 200                 205

Ser Thr Ser Pro Thr Tyr Phe Gly Arg Pro Tyr Gln His His Asp Gly
210                 215                 220

Gln Thr Asp Ala Ser Asn Gly Ala Asn Tyr Ile Thr Met Ser Tyr Asn
225                 230                 235                 240

Tyr Tyr His Asp His Asp Lys Ser Ser Ile Phe Gly Ser Ser Asp Ser
            245                 250                 255

Lys Ile Ser Asp Asp Gly Lys Leu Lys Ile Thr Leu His His Asn Arg
            260                 265                 270

Tyr Lys Asn Ile Val Gln Arg Ala Pro Arg Val Arg Phe Gly Gln Val
            275                 280                 285

His Val Tyr Asn Asn Tyr Tyr Glu Gly Ser Thr Ser Ser Ser Asp Tyr
            290                 295                 300

Pro Phe Ser Tyr Ala Trp Gly Ile Gly Lys Ser Ser Lys Ile Tyr Ala
305                 310                 315                 320

Gln Asn Asn Val Ile Asp Val Pro Gly Leu Pro Ala Ala Lys Thr Ile
            325                 330                 335

Lys Val Phe Ser Gly Gly Thr Ala Leu Tyr Asp Ser Gly Thr Leu Leu
            340                 345                 350

Asn Gly Thr Gln Ile Asn Ala Ser Ala Ala Asn Gly Leu Ser Ser Ser
            355                 360                 365

Val Gly Trp Thr Pro Ser Leu His Gly Thr Ile Asp Ala Ser Ala His
            370                 375                 380

Val Lys Ser Asn Val Ile Ser Gln Ala Gly Ala Gly Lys Leu Asn
385                 390                 395

<210> SEQ ID NO 2
<211> LENGTH: 399
<212> TYPE: PRT
<213> ORGANISM: B. subtilis

<400> SEQUENCE: 2

Ala Asp Leu Gly His Gln Thr Leu Gly Ser Asn Asp Gly Trp Gly Ala
1               5                   10                  15

Tyr Ser Thr Gly Thr Thr Gly Gly Ser Lys Ala Ser Ser Asn Val
                20                  25                  30

Tyr Thr Val Ser Asn Arg Asn Gln Leu Val Ser Ala Leu Gly Lys Glu
            35                  40                  45

Thr Asn Thr Thr Pro Lys Ile Ile Tyr Ile Lys Gly Thr Ile Asp Met
50                  55                  60

Asn Val Asp Asp Asn Leu Lys Pro Leu Gly Leu Asn Asp Tyr Lys Asp
65                  70                  75                  80

Pro Glu Tyr Asp Leu Asp Lys Tyr Leu Lys Ala Tyr Asp Pro Ser Thr
                85                  90                  95

Trp Gly Lys Lys Glu Pro Ser Gly Thr Gln Glu Glu Ala Arg Ala Arg
            100                 105                 110

Ser Gln Lys Asn Gln Lys Ala Arg Val Met Val Asp Ile Pro Ala Asn
            115                 120                 125

Thr Thr Ile Val Gly Ser Gly Thr Asn Ala Lys Val Val Gly Gly Asn
            130                 135                 140

Phe Gln Ile Lys Ser Asp Asn Val Ile Ile Arg Asn Ile Glu Phe Gln
145                 150                 155                 160
```

```
Asp Ala Tyr Asp Tyr Phe Pro Gln Trp Asp Pro Thr Asp Gly Ser Ser
            165                 170                 175

Gly Asn Trp Asn Ser Gln Tyr Asp Asn Ile Thr Ile Asn Gly Gly Thr
            180                 185                 190

His Ile Trp Ile Asp His Cys Thr Phe Asn Asp Gly Ser Arg Pro Asp
            195                 200                 205

Ser Thr Ser Pro Lys Tyr Tyr Gly Arg Lys Tyr Gln His His Asp Gly
            210                 215                 220

Gln Thr Asp Ala Ser Asn Gly Ala Asn Tyr Ile Thr Met Ser Tyr Asn
225                 230                 235                 240

Tyr Tyr His Asp His Asp Lys Ser Ser Ile Phe Gly Ser Ser Asp Ser
            245                 250                 255

Lys Thr Ser Asp Asp Gly Lys Leu Lys Ile Thr Leu His His Asn Arg
            260                 265                 270

Tyr Lys Asn Ile Val Gln Arg Ala Pro Arg Val Arg Phe Gly Gln Val
            275                 280                 285

His Val Tyr Asn Asn Tyr Tyr Glu Gly Ser Thr Ser Ser Ser Ser Tyr
            290                 295                 300

Pro Phe Ser Tyr Ala Trp Gly Ile Gly Lys Ser Ser Lys Ile Tyr Ala
305                 310                 315                 320

Gln Asn Asn Val Ile Asp Val Pro Gly Leu Ser Ala Ala Lys Thr Ile
                    325                 330                 335

Ser Val Phe Ser Gly Gly Thr Ala Leu Tyr Asp Ser Gly Thr Leu Leu
                340                 345                 350

Asn Gly Thr Gln Ile Asn Ala Ser Ala Ala Asn Gly Leu Ser Ser Ser
            355                 360                 365

Val Gly Trp Thr Pro Ser Leu His Gly Ser Ile Asp Ala Ser Ala Asn
370                 375                 380

Val Lys Ser Asn Val Ile Asn Gln Ala Gly Ala Gly Lys Leu Asn
385                 390                 395
```